US011857348B2

(12) United States Patent
Field et al.

(10) Patent No.: US 11,857,348 B2
(45) Date of Patent: Jan. 2, 2024

(54) TECHNIQUES FOR DETERMINING A TIMING UNCERTAINTY OF A COMPONENT OF AN OPTICAL MEASUREMENT SYSTEM

(71) Applicant: HI LLC, Los Angeles, CA (US)

(72) Inventors: Ryan Field, Culver City, CA (US); Bruno Do Valle, Brighton, MA (US); Jacob Dahle, Arlington, MA (US); Sebastian Sorgenfrei, Playa Vista, CA (US)

(73) Assignee: HI LLC, Los Angeles, CA (US)

(*) Notice: Subject to any disclaimer, the term of this patent is extended or adjusted under 35 U.S.C. 154(b) by 306 days.

(21) Appl. No.: 17/202,583

(22) Filed: Mar. 16, 2021

(65) Prior Publication Data
US 2021/0290169 A1    Sep. 23, 2021

Related U.S. Application Data

(60) Provisional application No. 63/044,521, filed on Jun. 26, 2020, provisional application No. 62/992,499, filed on Mar. 20, 2020.

(51) Int. Cl.
A61B 5/00    (2006.01)

(52) U.S. Cl.
CPC .......... A61B 5/7214 (2013.01); A61B 5/0082 (2013.01); A61B 5/6803 (2013.01); A61B 2562/0238 (2013.01); A61B 2562/046 (2013.01); A61B 2576/026 (2013.01)

(58) Field of Classification Search
CPC .... A61B 5/00; A61B 5/68; A61B 5/40; G06T 1/00; G06T 5/00; G06V 10/00
USPC ............... 250/214 R, 214.1, 208.1
See application file for complete search history.

(56) References Cited

U.S. PATENT DOCUMENTS

| | | | |
|---|---|---|---|
| 4,018,534 A | 4/1977 | Thorn et al. |
| 4,207,892 A | 6/1980 | Binder |
| 4,281,645 A | 8/1981 | Jobsis |
| 4,321,930 A | 3/1982 | Jobsis |

(Continued)

FOREIGN PATENT DOCUMENTS

| | | |
|---|---|---|
| CN | 200950235 | 9/2007 |
| CN | 107865635 | 4/2018 |

(Continued)

OTHER PUBLICATIONS

Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680, Oct. 29, 2018.

(Continued)

Primary Examiner — Que Tan Le
(74) Attorney, Agent, or Firm — ALG Intellectual Property, LLC

(57) ABSTRACT

An exemplary optical measurement system includes a signal generator configured to generate a signal and a processing unit configured to direct the signal generator to apply the signal to a component within the optical measurement system, generate, based on a response of the component to the signal, characterization data representative of a timing uncertainty associated with the component, and perform, based on the characterization data, an action associated with the component.

18 Claims, 23 Drawing Sheets

(56) References Cited

U.S. PATENT DOCUMENTS

| | | |
|---|---|---|
| 4,515,165 A | 5/1985 | Carroll |
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,240,309 B1 | 5/2001 | Yamashita et al. |
| 6,384,663 B2 | 5/2002 | Cova et al. |
| 6,541,752 B2 | 4/2003 | Zappa et al. |
| 6,618,614 B1 | 9/2003 | Chance |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,634,826 B1 | 4/2017 | Park |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | Mcgarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 9,997,551 B2 | 6/2018 | Mandai et al. |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |
| 10,515,993 B2 | 12/2019 | Field et al. |
| 10,533,893 B2 | 1/2020 | Leonardo |
| 10,558,171 B2 | 2/2020 | Kondo |
| 10,594,306 B2 | 3/2020 | Dandin |
| 10,627,460 B2 | 4/2020 | Alford et al. |
| 10,695,167 B2 * | 6/2020 | Van Heugten ........ A61F 2/1624 |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | JiméNez-Martínez |
| 10,996,293 B2 | 5/2021 | Mohseni |
| 11,006,876 B2 | 5/2021 | Johnson |
| 11,006,878 B2 | 5/2021 | Johnson |
| 2002/0195545 A1 | 12/2002 | Nishimura |
| 2004/0057478 A1 | 3/2004 | Saito |
| 2004/0078216 A1 | 4/2004 | Toto |
| 2004/0160996 A1 | 8/2004 | Giorgi et al. |
| 2005/0038344 A1 | 2/2005 | Chance |
| 2005/0061986 A1 | 3/2005 | Kardynal et al. |
| 2005/0124863 A1 | 6/2005 | Cook |
| 2005/0228291 A1 | 10/2005 | Chance |
| 2006/0171845 A1 | 8/2006 | Martin |
| 2006/0197452 A1 | 9/2006 | Zhang |

(56) References Cited

U.S. PATENT DOCUMENTS

| | | |
|---|---|---|
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0054789 A1 | 2/2009 | Kiguchi et al. |
| 2009/0163775 A1 | 6/2009 | Barrett |
| 2009/0313048 A1 | 12/2009 | Kahn et al. |
| 2010/0210952 A1 | 8/2010 | Taira et al. |
| 2010/0249557 A1 | 9/2010 | Besko et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1 | 4/2012 | Al-Ali et al. |
| 2012/0101838 A1 | 4/2012 | Ingard et al. |
| 2013/0015331 A1 | 1/2013 | Birk |
| 2013/0030267 A1 | 1/2013 | Lisogurski |
| 2013/0030270 A1 | 1/2013 | Chiou et al. |
| 2013/0032713 A1 | 2/2013 | Barbi et al. |
| 2013/0090541 A1 | 4/2013 | Macfarlane et al. |
| 2013/0144644 A1 | 6/2013 | Simpson |
| 2013/0221221 A1 | 8/2013 | Bouzid et al. |
| 2013/0225953 A1 | 8/2013 | Oliviero et al. |
| 2013/0342835 A1 | 12/2013 | Blacksberg |
| 2014/0027607 A1 | 1/2014 | Mordarski et al. |
| 2014/0028211 A1 | 1/2014 | Imam |
| 2014/0055181 A1 | 2/2014 | Chavpas |
| 2014/0066783 A1 | 3/2014 | Kiani |
| 2014/0171757 A1 | 6/2014 | Kawato et al. |
| 2014/0185643 A1 | 7/2014 | Mccomb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | Mcgarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | Mcgarvey et al. |
| 2017/0052065 A1 | 2/2017 | Sharma et al. |
| 2017/0085547 A1 | 3/2017 | De Aguiar et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1 | 6/2017 | Soulet De Brugiere |
| 2017/0176579 A1 | 6/2017 | Niclass et al. |
| 2017/0176596 A1 | 6/2017 | Shpunt et al. |
| 2017/0179173 A1 | 6/2017 | Mandal et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1 | 5/2018 | Kuzniecky |
| 2018/0120152 A1 | 5/2018 | Eonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0200888 A1 | 7/2019 | Poltorak |
| 2019/0209012 A1 | 7/2019 | Yoshimoto et al. |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1 | 1/2020 | Vanegas |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0060542 A1 | 2/2020 | Alford |
| 2020/0088811 A1 | 3/2020 | Mohseni |

(56) References Cited

U.S. PATENT DOCUMENTS

| | | |
|---|---|---|
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson et al. |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

Bellis, et al.,"Photon counting imaging: the DigitalAPD," Society of Photo-Optical Instrumentation Engineers (SPIE) Conference Series, Feb. 2006, vol. 6068, pp. 111-120.

Blutman, et al.,"A 0.1 pJ Freeze Vernier Time-to-Digital Converter in 65nm CMOS," 2014 International Symposium on Circuits and Systems (ISCAS), Melbourne, Australia, Jun. 1-5, 2014.

Cambie, et al.,"Every photon counts: understanding and optimizing photon paths in luminescent solar concentrator-based photomicroreactors (LSC-PMs)," React. Chem. Eng., 2017, 2, 561-566.

Contini, et al.,"Photon migration through a turbid slab described by a model based on diffusion approximation. I. Theory," Appl. Opt. 36(19), 4587 (1997).

Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.

Dalla Mora, et al., "Memory effect in silicon time-gated single-photon avalanche diodes," http://dx.doi.org/10.1063/1.4915332, Journal of Applied Physics 117, 114501, 2015.

De Heyn, et al.,"A fast start-up 3GHZ-10GHz digitally controlled oscillator for UWB impulse radio in 90nm CMOS," 2007 European Solid-State Circuits Conference—(ESSCIRC), Munich, Germany, pp. 484-487, Sep. 11-13, 2007.

Di Sieno, et al., "Probe-hosted large area silicon photomultiplier and high-throughput timing electronics for enhanced performance time-domain functional near-infrared spectroscopy," Biomed. Opt. Express 11(11), 6389 (2020).

Dutton, et al.,"A Time-Correlated Single-Photon-Counting Sensor with 14GS/s Histogramming Time-to-Digital Converter," 2015 IEEE International Solid-State Circuits Conference ISSCC 2015 / SESSION 11 / Sensors and Imagers for Life Sciences / 11.5, Feb. 22-26, 2015.

Fishburn, et al., "Temporal Derivative Distribution Repair (TDDR): A motion correction method for fNIRS," Neuroimage. Jan. 1, 2019; 184: 171-179. doi:10.1016/j.neuroimage.2018.09.025.

Fisher, et al.,"A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al.,"Progress in Quenching Circuits for Single Photon Avalanche Diodes," IEEE Transactions on Nuclear Science, vol. 57, No. 6, Dec. 2010.

Gnecchi, et al.,"A 1×16 SIPM Array for Automotive 3D Imaging LIDAR Systems.", Proceedings of the 2017 International Image Sensor Workshop (IISW), Hiroshima, Japan (2017).

Harmon, et al.,"Compound Semiconductor SPAD Arrays," LightSpin Technologies, http://www.lightspintech.com/publications.html (2013).

Henderson, et al.,"A 192 × 128 Time Correlated SPAD Image Sensor in 40-nm CMOS Technology," IEEE Journal of Solid-State Circuits, 2019.

Henderson, et al.,"A 256×256 40nm/90nm CMOS 3D-Stacked 120dB Dynamic-Range Reconfigurable Time-Resolved SPAD Imager," 2019 IEEE International Solid- State Circuits Conference—(ISSCC), San Francisco, CA, USA, 2019, pp. 106-108. doi: 10.1109/ISSCC.2019.8662355.

Huppert, et al.,"HomER: a review of time-series analysis methods for near-infrared spectroscopy of the brain," Appl. Opt. 48(10), D280 (2009).

Kienle, et al.,"Improved solutions of the steady-state and the time-resolved diffusion equations for reflectance from a semi-infinite turbid medium," J. Opt. Soc. Am. A 14(1), 246 (1997).

Konugolu, et al.,"Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al.,"Wearable and wireless time-domain near-infrared spectroscopy system for brain and muscle hemodynamic monitoring," Biomed. Opt. Express 11(10), 5934 (2020).

Lange, et al.,"Clinical Brain Monitoring with Time Domain NIRS: A Review and Future Perspectives," Applied Sciences 9(8), 1612 (2019).

Lange, et al.,"Maestros: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Lee, et al.,"High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al.,"A 4 × 4 × 416 digital SiPM array with 192 TDCs for multiple high-resolution timestamp acquisition," 2013 JINST 8 PO5024, May 31, 2013.

Martelli, et al.,"Optimal estimation reconstruction of the optical properties of a two-layered tissue phantom from time-resolved single-distance measurements," Journal of Biomedical Optics 20(11), 115001 (Nov. 2015).

(56) References Cited

OTHER PUBLICATIONS

Maruyama, et al.,"A 1024 × 8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014.

Mita, et al.,"High-Speed and Compact Quenching Circuit for Single-Photon Avalanche Diodes," IEEE Transactions on Instrumentation and Measurement, vol. 57, No. 3, Mar. 2008. pp. 543-547.

Mora, et al.,"Fast silicon photomultiplier improves signal harvesting and reduces complexity in time-domain diffuse optics," Opt. Express 23(11), 13937 (2015).

Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al.,"A 256 × 256 SPAD array with in-pixel Time to Amplitude Conversion for Fluorescence Lifetime Imaging Microscopy," *Memory 900.M4*, 2015.

Pifferi, et al.,"Performance assessment of photon migration instruments: the MEDPHOT protocol," Applied Optics, 44(11), 2104-2114 (2005).

Prahl, et al.,"Optical Absorption of Hemoglobin," http://omic.ogi.edu/spectra/hemoglobin/index.html (1999).

Puszka, et al.,"Time-resolved diffuse optical tomography using fast-gated single-photon avalanche diodes," Biomedical optics express, 2013, vol. 4, No. 8, pp. 1351-1365 (Year: 2013).

Re, et al.,"Multi-channel medical device for time domain functional near infrared spectroscopy based on wavelength space multiplexing," Biomed. Opt. Express 4(10), 2231 (2013).

Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).

Richardson, et al.,"A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.

Takai, et al.,"Single-Photon Avalanche Diode with Enhanced NIR-Sensitivity for Automotive LIDAR Systems," Sensors, 2016, 16(4): 459, pp. 1-9 (Year: 2016).

Torricelli, et al.,"Time domain functional NIRS imaging for human brain mapping," Neuroimage 85, 28-50 (2014).

Wabnitz, et al.,"Depth-selective data analysis for time-domain fNIRS; moments vs. time windows," Biomed. Opt. Express 11(8), 4224 (2020).

Wabnitz, et al.,"Performance assessment of time-domain optical brain imagers, part 1: basic instrumental performance protocol," Journal of Biomedical Optics 19(8), 086010 (Aug. 2014).

Wabnitz, et al.,"Performance assessment of time-domain optical brain imagers, part 2: nEUROPt protocol," Journal of Biomedical Optics 19(8), 086012 (Aug. 2014).

Wojtkiewicz, et al.,"Self-calibrating time-resolved near infrared spectroscopy," Biomed. Opt. Express 10(5), 2657 (2019).

Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016 Nov. 17, 2018.

Zucchelli, et al.,"Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.

International Search Report and Written Opinion received in International Application No. PCT/2020/027537, dated Sep. 7, 2020.

International Search Report and Written Opinion received in International Application No. PCT/2020/028820, dated Aug. 26, 2020.

International Search Report and Written Opinion received in International Application No. PCT/US20/34062, dated Aug. 26, 2020.

International Search Report and Written Opinion received in International Application No. PCT/US2018/058580, dated Feb. 12, 2019.

International Search Report and Written Opinion received in International Application No. PCT/US2018/062777, dated Feb. 13, 2019.

International Search Report and Written Opinion received in International Application No. PCT/US2019/019317, dated May 28, 2019.

Non-Final Office Action received in U.S. Appl. No. 16/177,351, dated Apr. 1, 2019.

Non-Final Office Action received in U.S. Appl. No. 16/283,730, dated May 16, 2019.

Non-Final Office Action received in U.S. Appl. No. 16/370,991, dated Feb. 10, 2020.

Non-Final Office Action received in U.S. Appl. No. 16/537,360, dated Feb. 25, 2020.

Non-Final Office Action received in U.S. Appl. No. 16/544,850, dated Jun. 25, 2020.

Non-Final Office Action received in U.S. Appl. No. 16/856,524, dated Dec. 1, 2020.

Partial Search Report received in International Application No. PCT/2020/028820, dated Jul. 1, 2020.

Partial Search Report received in International Application No. PCT/US2020/027537, dated Jul. 17, 2020.

Chen, et al., "A PVT Insensitive Field Programmable Gate Array Time-to-digital Converter", 2013 IEEE Nordic-Mediterranean Workshop on Time-To-Digital Converters. Oct. 3, 2013.

Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.

Lebid, et al., "Multi-Timescale Measurements of Brain Responses in Visual Cortex During Functional Stimulation Using Time-Resolved Spectroscopy", SPIE vol. 5826. Dec. 31, 2005. p 609, last paragraph—p. 610, paragraph 1.

Zheng, et al., "An Integrated Bias Voltage Control Method for SPAD Arrays", Oct. 1, 2018, IEEE Service Center.

"emojipedia.org", https://emojipedia.org (accessed May 27, 2021).

"International Search Report and Written Opinion received in International Application No. PCT/2021/018188".

"International Search Report and Written Opinion received in International Application No. PCT/US2021/018155".

"International Search Report and Written Opinion received in International Application No. PCT/US2021/018187".

"International Search Report and Written Opinion received in International Application No. PCT/US2021/018190".

"scienceofpeople.com/emojis", https://www.scienceofpeople.com/emojis/ (accessed May 27, 2021).

Hebert, et al.,"Spatiotemporal image correlation spectroscopy (STICS) theory, verification, and application to protein velocity mapping in living CHO cells", Biophysical journal 88, No. 5 (2005): 3601-3614.

Kheng, et al.,"Image Processing", https://www.comp.nus.edu.sg/~cs4243/lecture/imageproc.pdf, Mar. 9, 2014.

Sneha, et al.,"Understanding Correlation", https://www.allaboutcircuits.com/technical-articles/understanding- correlation/, Jan. 4, 2017.

Ku, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.

Zucconi, et al.,"The Autocorrelation Function", https://www.alanzucconi.com/2016/06/06/autocorrelation-function/, Jun. 6, 2016.

Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680.

Blutman, et al.,"A 0.1 pJ Freeze Vernier Time-to-Digital Converter in 65nm CMOS," 2014 International Symposium on Circuits and Systems (ISCAS), Melbourne, Australia.

De Heyn, et al.,"A fast start-up 3GHZ-10GHz digitally controlled oscillator for UWB impulse radio in 90nm CMOS," 2007 European Solid-State Circuits Conference—(ESSCIRC), Munich, Germany, pp. 484-487.

(56) References Cited

OTHER PUBLICATIONS

Dutton, et al., "A Time-Correlated Single-Photon-Counting Sensor with 14GS/s Histogramming Time-to-Digital Converter," 2015 IEEE International Solid-State Circuits Conference ISSCC 2015 / SESSION 11 / Sensors and Imagers for Life Sciences / 11.5.
Mandai, et al., "A 4 × 4 × 416 digital SiPM array with 192 TDCs for multiple high-resolution timestamp acquisition," 2013 JINST 8 PO5024.
Parmesan, et al., "A 256 × 256 SPAD array with in-pixel Time to Amplitude Conversion for Fluorescence Lifetime Imaging Microscopy," 2015.

\* cited by examiner

TECHNIQUES FOR DETERMINING A TIMING UNCERTAINTY OF A COMPONENT OF AN OPTICAL MEASUREMENT SYSTEM

RELATED APPLICATIONS

The present application claims priority under 35 U.S.C. § 119(e) to U.S. Provisional Patent Application No. 62/992,499, filed on Mar. 20, 2020, and to U.S. Provisional Patent Application No. 63/044,521, filed on Jun. 26, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Techniques for determining a timing uncertainty of a component of an optical measurement system are described herein.

A photodetector capable of capturing individual photons with very high time-of-arrival resolution (a few tens of picoseconds) is an example of a non-invasive detector that can be used in an optical measurement system to detect neural activity within a body (e.g., the brain). However, each photodetector in an array of photodetectors has timing uncertainty when it triggers a detected event. Moreover, each time-to-digital converter (TDC) in an array of TDCs has its own timing uncertainty, differential nonlinearity (DNL), and integral nonlinearity (INL) characteristics. Such timing uncertainties may be systematic (e.g., caused by manufacturing process variations, etc.) and/or random.

The systems, circuits, and methods described herein facilitate characterization of the timing uncertainty, such as nonlinearities and/or impulse response functions (e.g., jitter), of individual photodetectors, TDCs, and/or other components (e.g., other circuits of interest) within an optical measurement system. Based on this characterization, various actions may be performed. For example, systems, circuits, and/or methods described herein may compensate for the timing uncertainty associated with a particular component, rate (e.g., grade an effectiveness of) a particular component, and/or selectively disable a particular component so that measurement results (e.g., histograms) output by the optical measurement system are not skewed or otherwise affected by the timing uncertainties of a particular component. This may make the photon detection operation of the optical measurement system more accurate and effective.

These and other advantages and benefits of the present systems, circuits, and methods are described more fully herein.

Figure 1:
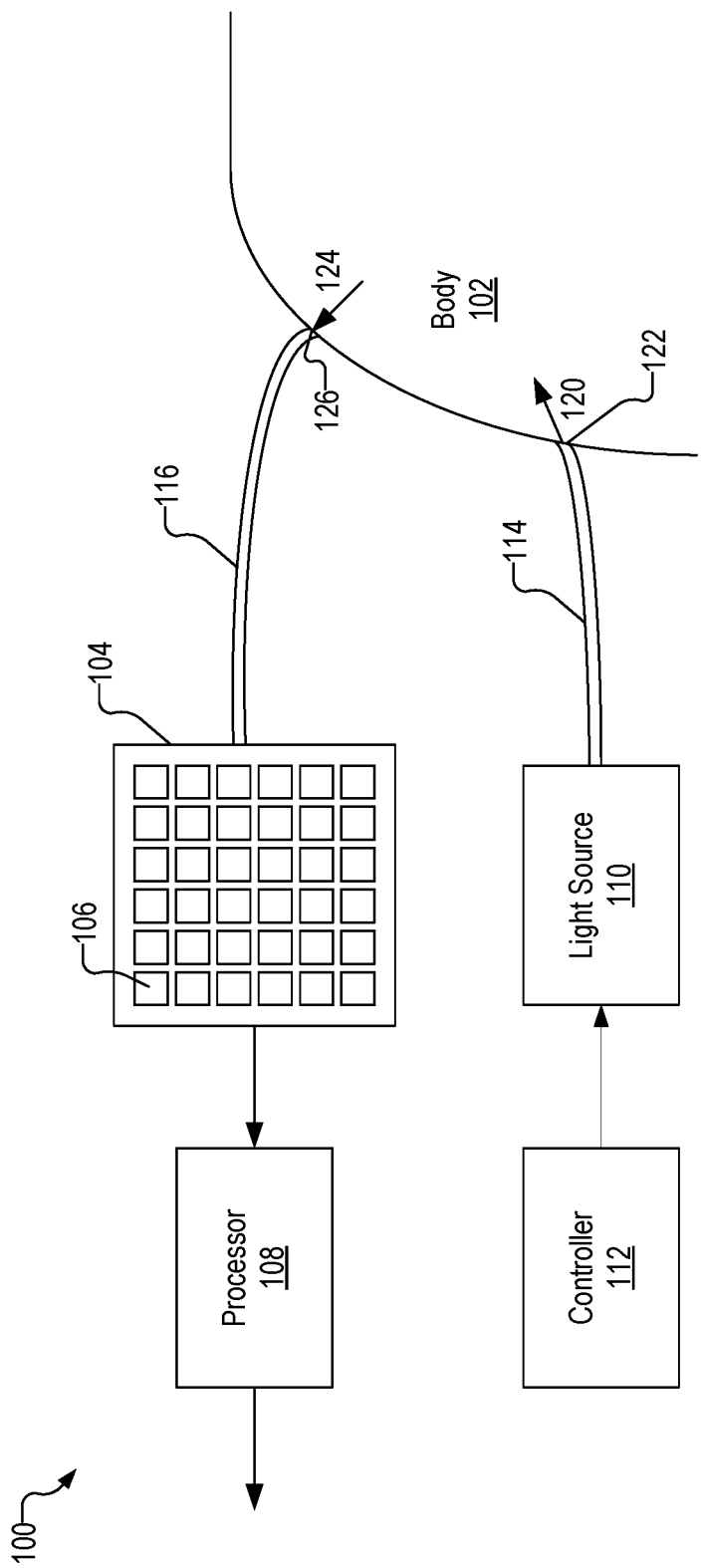
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
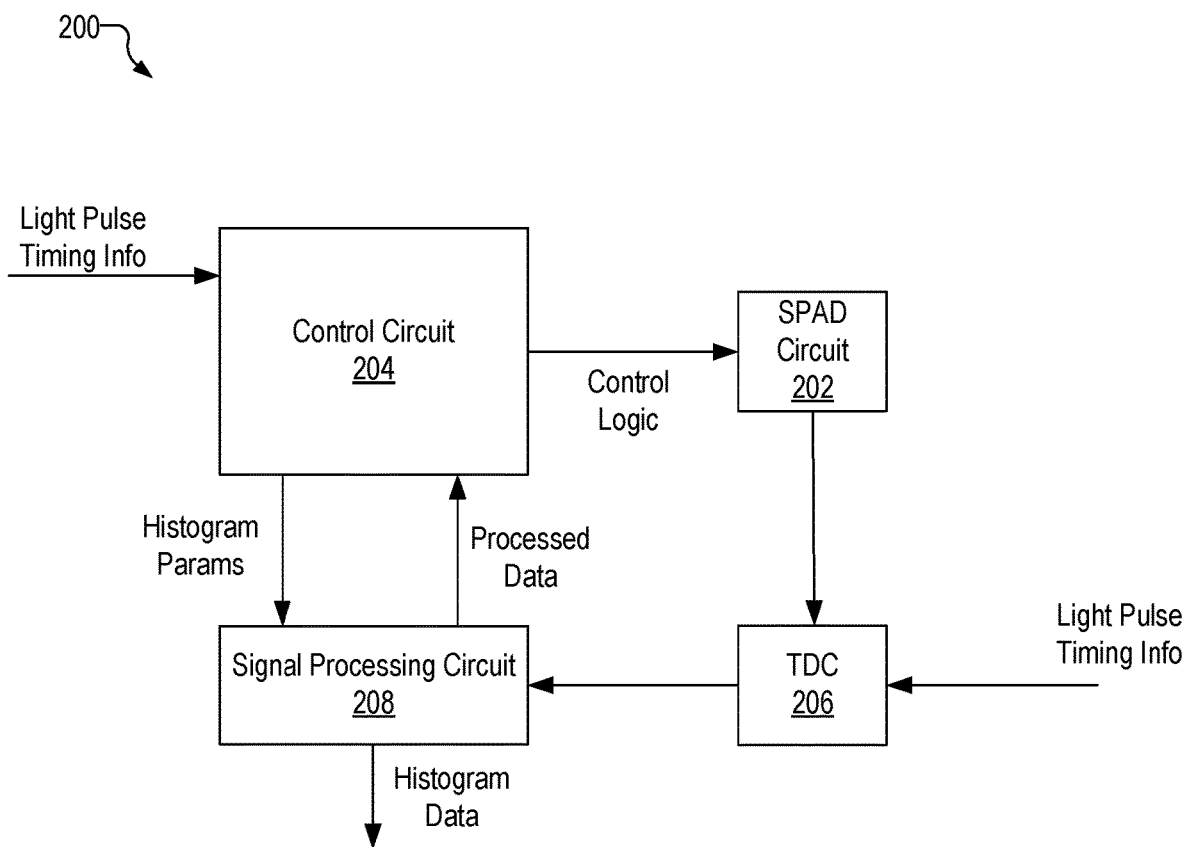
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their respective entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
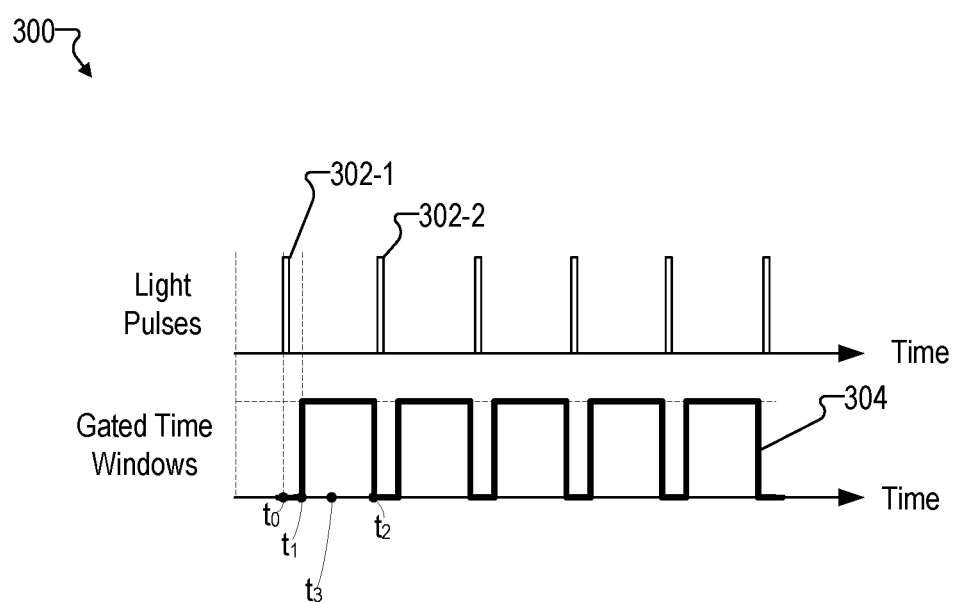
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
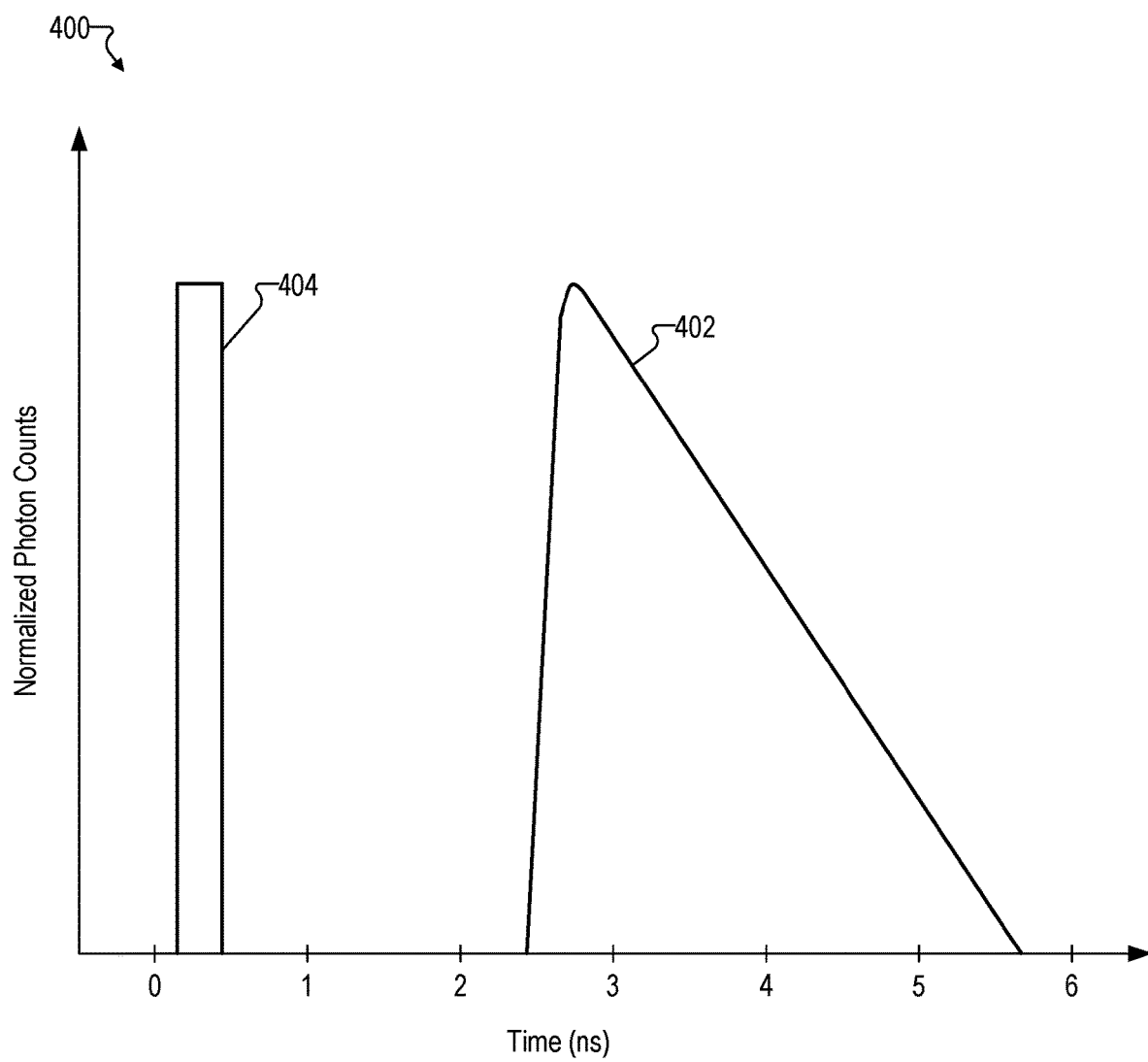
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
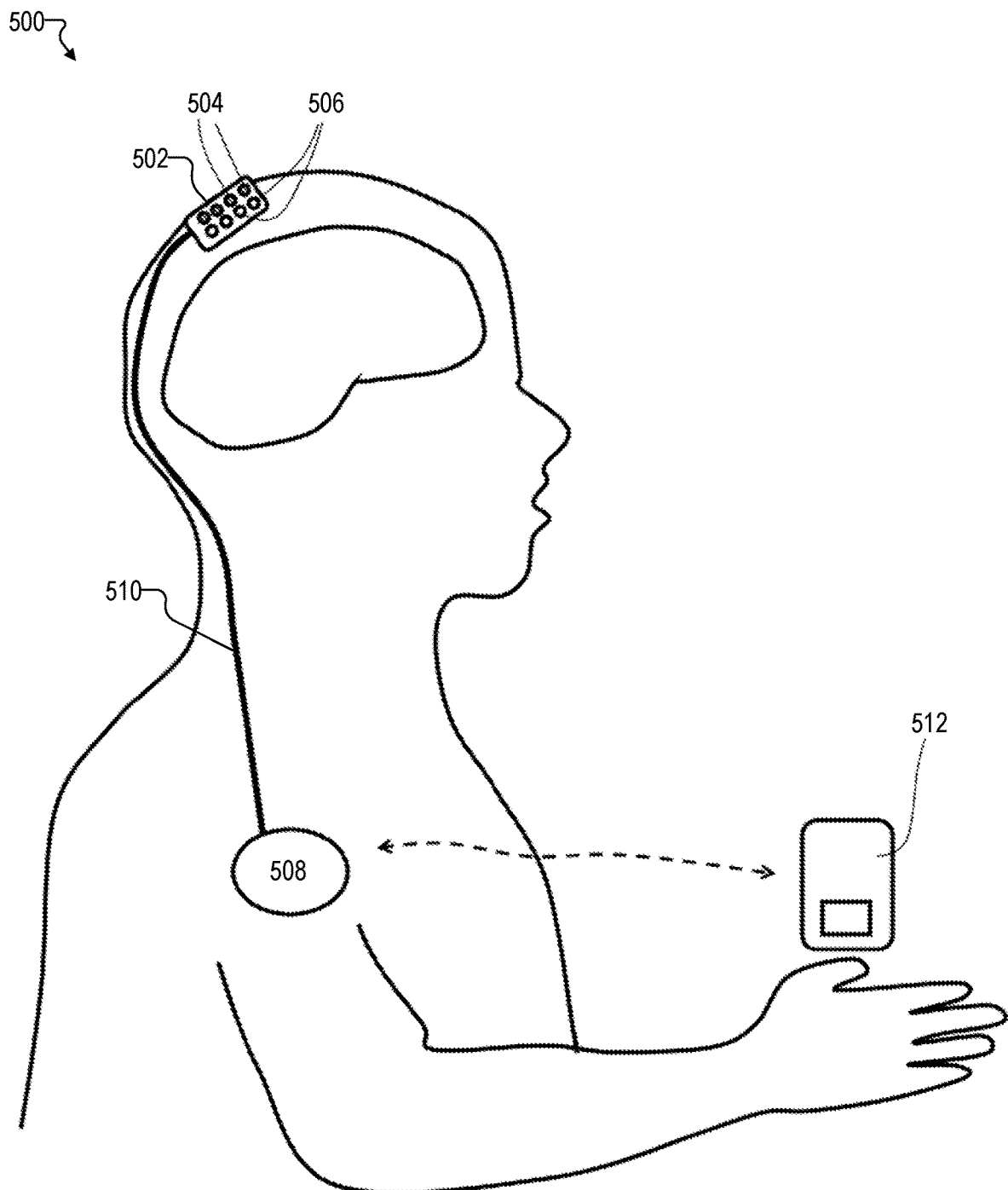
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by photodetector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
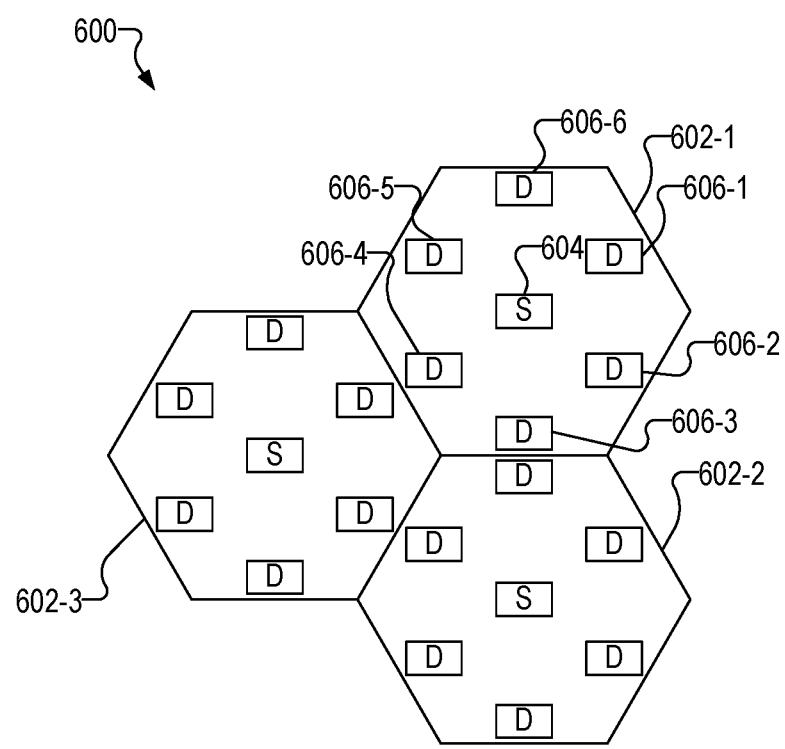
FIG. 6 shows an exemplary wearable module assembly.

To illustrate, FIG. 6 shows an exemplary wearable module assembly 600 ("assembly 600") that implements one or more of the optical measurement features described herein. Assembly 600 may be worn on the head or any other suitable body part of the user. As shown, assembly 600 may include a plurality of modules 602 (e.g., modules 602-1 through 602-3). While three modules 602 are shown to be included in assembly 600 in FIG. 6, in alternative configurations, any number of modules 602 (e.g., a single module up to sixteen or more modules) may be included in assembly 600. Moreover, while modules 602 are shown to be adjacent to and touching one another, modules 602 may alternatively be spaced apart from one another (e.g., in implementations where modules 602 are configured to be inserted into individual slots or cutouts of the headgear). Moreover, while modules 602 are shown to have a hexagonal shape, modules 602 may alternatively have any other suitable geometry (e.g., in the shape of a pentagon, octagon, square, rectangular, circular, triangular, free-form, etc.). Assembly 600 may conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, which application is incorporated herein by reference in its entirety.

Each module 602 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors (e.g., SPADs) as well as other circuitry (e.g., TDCs). As shown, detectors 606 are arranged around and substantially equidistant from source 604. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light emitter and the detector allows subsequent processing of the detected signals to infer spatial (e.g., depth localization, inverse modeling) information about the detected signals. Detectors 606 may be alternatively disposed as may serve a particular implementation.

Figure 7:
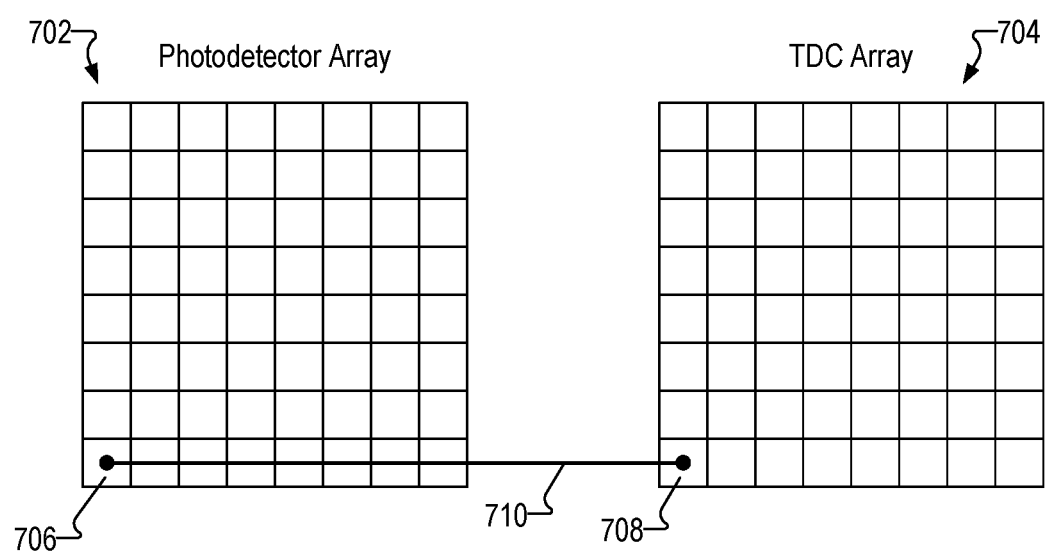
FIG. 7 shows an exemplary photodetector array and a corresponding time-to-digital converter array that may be included in an optical measurement system.

FIG. 7 shows an exemplary photodetector array 702 and a corresponding TDC array 704 that may be included in an optical measurement system (e.g., optical measurement system 100).

As shown, photodetector array 702 may include a plurality of photodetectors (e.g., photodetector 706). Each photodetector may be similar to any of the photodetectors described herein. For example, each photodetector may be implemented by a SPAD. In some examples, photodetector array 702 is included in a detector (e.g., one of detectors 606 shown in FIG. 6) located on a module (e.g., one of modules 602 shown in FIG. 6).

TDC array 704 may include a plurality of TDCs (e.g., TDC 708). Each TDC may be similar to any of the TDCs described herein and may correspond to a different one of the photodetectors included in photodetector array 702. For example, TDC 708 corresponds to photodetector 706 (i.e., TDC 708 is configured to detect photon arrival times for photodetector 706). To detect a photon arrival time, TDC 708 may be configured to detect a photodetector output pulse generated by photodetector 706 when photodetector 706 detects a photon and, in response, record a timestamp symbol when the photodetector output pulse is detected. The timestamp symbol may, for example, be a multi-bit data sequence or code that represents an amount of elapsed time between when a light pulse including the photon is emitted and when TDC 708 detects the photodetector output pulse. A propagation time between when photodetector 706 detects a photon and TDC 708 records a corresponding timestamp symbol is represented in FIG. 7 by line 710. This propagation time may be different for different TDC/photodetector pairs due to different timing uncertainties associated with each individual photodetector and TDC.

The systems, circuits, and methods described herein may be configured to characterize (e.g., determine electrical characteristics of) a timing uncertainty of any of the photodetectors included in photodetector array 702, any of the TDCs included in TDC array 704, and/or any other component included in the optical measurement system 100. In this manner, the systems, circuits, and methods described herein may characterize all or a portion of a propagation time (e.g., the propagation time represented by line 710) between when a photodetector detects a photon and a corresponding TDC records a timestamp symbol.

Figure 8:
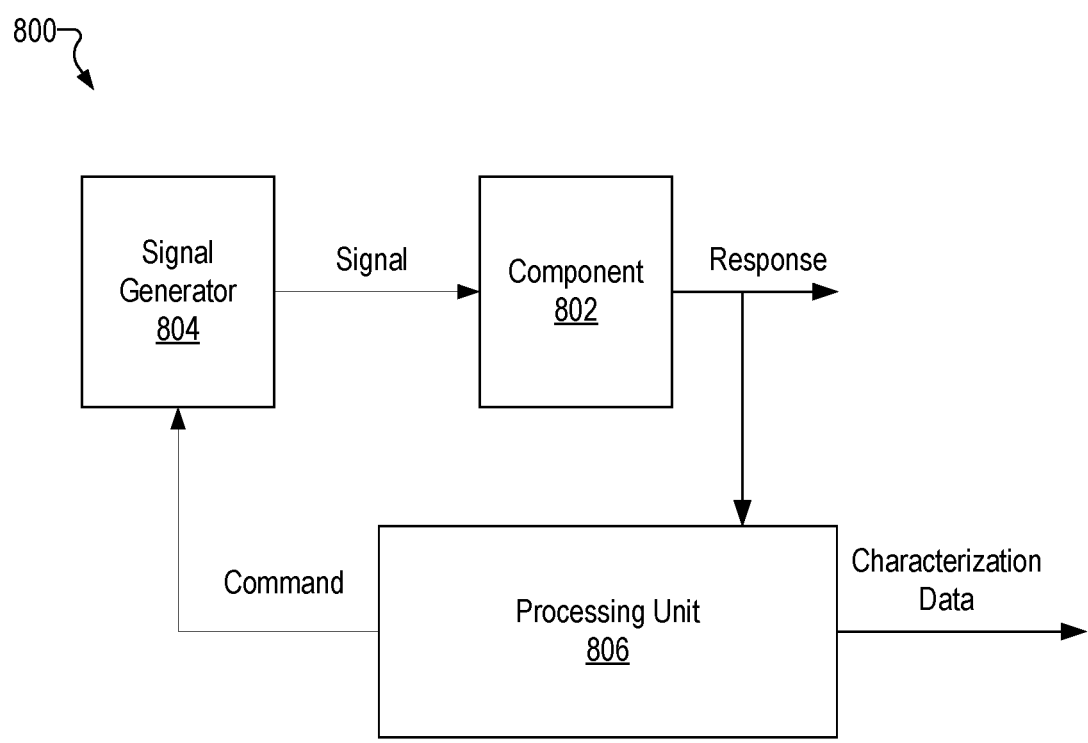
FIG. 8 shows an exemplary configuration that may be used to characterize a timing uncertainty of a component included in an optical measurement system

FIG. 8 shows an exemplary configuration 800 that may be used to characterize a timing uncertainty of a component 802 included in an optical measurement system. Component 802 may include a photodetector, a TDC, and/or any other circuit of interest within the optical measurement system. As shown, configuration 800 may include a signal generator 804 and a processing unit 806 in communication one with another.

Signal generator 804 may be implemented by any suitable circuitry configured to generate a signal (e.g., an electrical signal or an optical signal) that may be applied to component 802. Illustrative implementations of signal generator 804 are described herein.

Processing unit 806 may be implemented by processor 108, controller 112, control circuit 204, and/or any other suitable processing and/or computing device or circuit.

Figure 9:
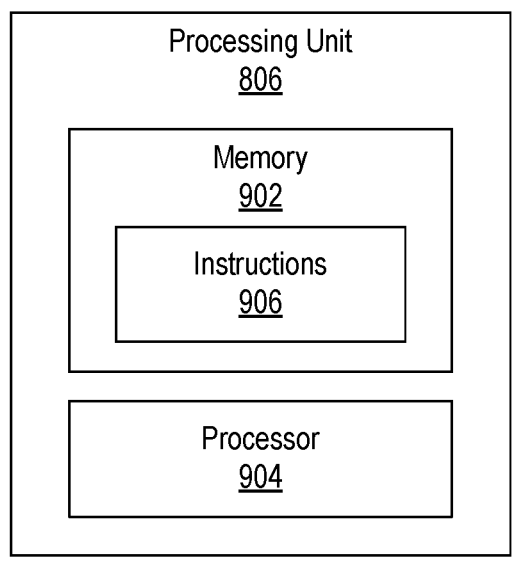
FIG. 9 illustrates an exemplary processing unit.

For example, FIG. 9 illustrates an exemplary implementation of processing unit 806 in which processing unit 806 includes a memory 902 and a processor 904 configured to be selectively and communicatively coupled to one another. In some examples, memory 902 and processor 904 may be distributed between multiple devices and/or multiple locations as may serve a particular implementation.

Memory 902 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 902 may maintain (e.g., store) executable data used by processor 904 to perform one or more of the operations described herein. For example, memory 902 may store instructions 906 that may be executed by processor 904 to perform any of the operations described herein. Instructions 906 may be implemented by any suitable application, program (e.g., sound processing program), software, code, and/or other executable data instance. Memory 902 may also maintain any data received, generated, managed, used, and/or transmitted by processor 904.

Processor 904 may be configured to perform (e.g., execute instructions 906 stored in memory 902 to perform) various operations described herein. For example, processor 904 may be configured to perform any of the operations described herein as being performed by processing unit 806.

Returning to FIG. 8, as shown, processing unit 806 may be configured to transmit a command to signal generator 804 that directs signal generator 804 to apply a signal to component 802. Component 802 may be configured to generate a response to the applied signal. Exemplary responses are described herein. Processing unit 806 may detect the response and generate, based on the response, characterization data representative of a timing uncertainty associated with component 802. Based on the characterization data, processing unit 806 may perform an action associated with component 802. Examples of this are described herein.

Figure 10:
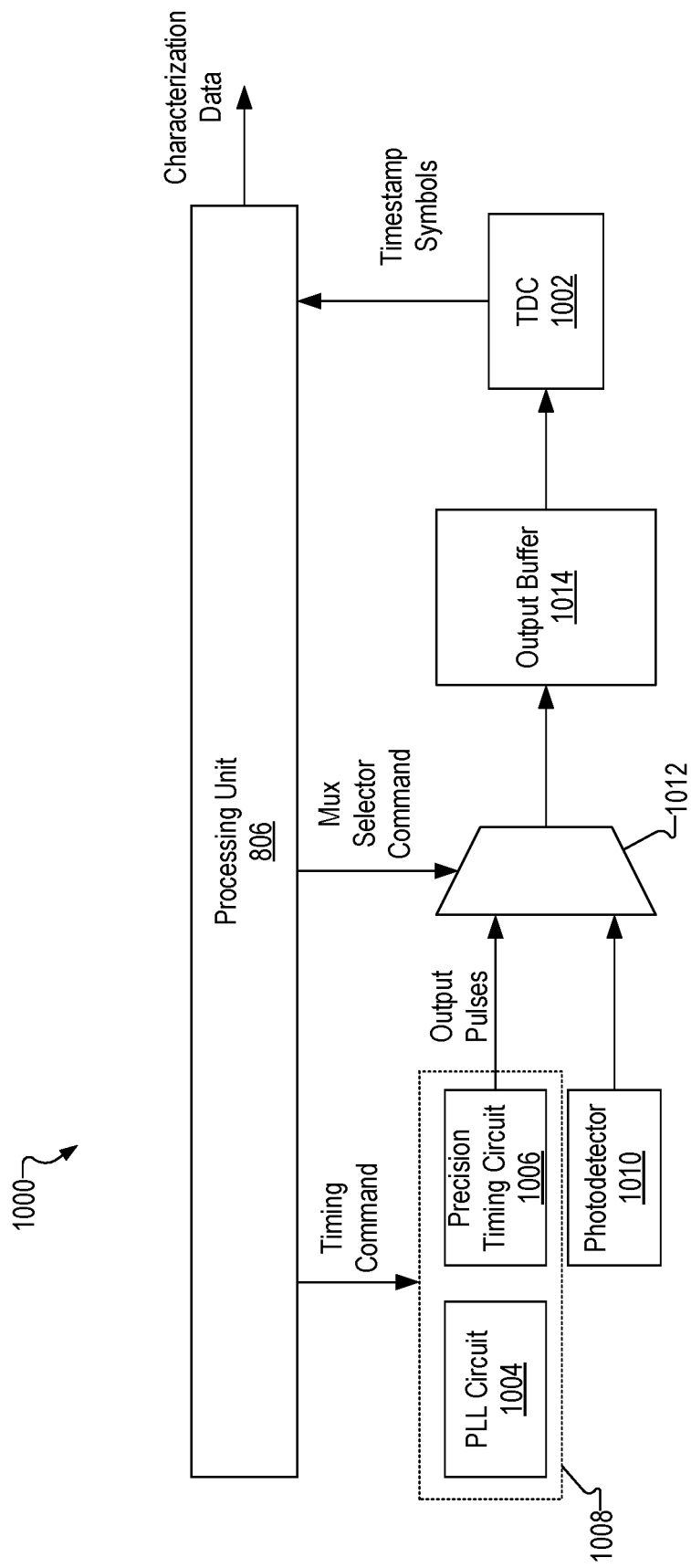
FIG. 10 shows an exemplary implementation of the configuration shown in FIG. 8.

FIG. 10 shows an exemplary implementation 1000 of configuration 800 in which component 802 is implemented by a TDC 1002 and signal generator 804 is implemented by a phase locked loop (PLL) circuit 1004 and a precision timing circuit 1006. PLL circuit 1004 and precision timing circuit 1006 together constitute a PLL circuit based architecture 1008. Implementation 1000 further includes a photodetector 1010, a multiplexer 1012, and an output buffer 1014.

TDC 1002 may be similar to any of the TDCs described herein and may correspond to photodetector 1010, which may be similar to any of the photodetectors described herein.

For example, TDC 1002 may be configured to measure a time difference between an occurrence of a light pulse and an occurrence of a photodetector output pulse generated by photodetector 1010, where the photodetector output pulse indicates that photodetector 1010 has detected a photon from the light pulse after the light pulse is scattered by a target.

Multiplexer 1012 is configured to selectively pass, to TDC 1002 (e.g., by way of output buffer 1014), output pulses generated by precision timing circuit 1006 or a photodetector output pulse output by photodetector 1010. Processing unit 806 may control multiplexer 1012 by providing a MUX selector command to multiplexer 1012. For example, the MUX selector command may cause multiplexer 1012 to selectively pass the output pulses generated by precision timing circuit 1006 to TDC 1002 when it desired to characterize a timing uncertainty of TDC 1002 (e.g., during a calibration mode).

As shown, output buffer 1014 is in series with an output of multiplexer 1012. In this configuration, the output of multiplexer 1012 is passed to TDC 1002 by way of output buffer 1014. In some alternative configurations, output buffer 1014 is omitted such that the output of multiplexer 1012 is passed directly to TDC 1002.

PLL circuit 1004 is configured to have a PLL feedback period. The output pulses generated by precision timing circuit 1006 may have programmable temporal positions within the PLL feedback period. These programmable temporal positions may be specified by a timing command provided by processing unit 806. In this manner, as described herein, the output pulses may be used to characterize a timing uncertainty of TDC 1002 (e.g., one or more nonlinearities of TDC 1002).

Figure 11:
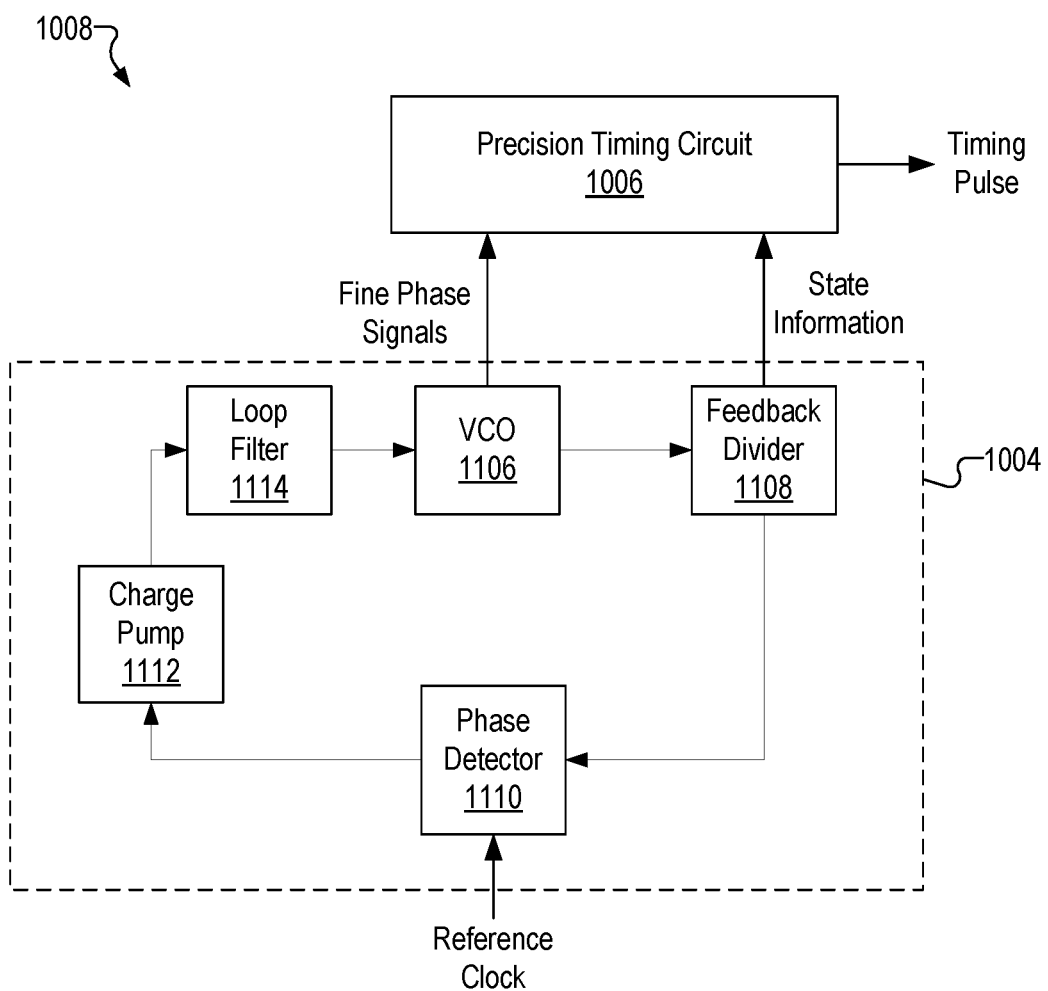
FIG. 11 illustrates an exemplary implementation of a phase locked loop circuit based architecture.

FIG. 11 illustrates an exemplary implementation of PLL circuit based architecture 1008. PLL circuit based architecture 1008 may be configured to generate and set a temporal position (e.g., of a rising edge and/or of a falling edge) of a timing pulse that may be used to set a temporal position of one or more output pulses described herein.

As shown, architecture 1008 includes PLL circuit 1004 communicatively coupled to precision timing circuit 1006. PLL circuit 1004 includes a VCO 1106, a feedback divider 1108, a phase detector 1110, a charge pump 1112, and a loop filter 1114 connected in a feedback loop configuration. Phase detector 1110 may receive a reference clock as an input such that PLL circuit 1004 has a PLL feedback period defined by the reference clock. The reference clock may have any suitable frequency, such as any frequency between 1 MHz and 200 MHz.

VCO 1106 may be implemented by any suitable combination of circuitry (e.g., a differential multi-stage gated ring oscillator (GRO) circuit) and is configured to lock to the reference clock (i.e., to a multiple of a frequency of the reference clock). To that end, VCO 1106 may include a plurality of stages configured to output a plurality of fine phase signals each having a different phase and uniformly distributed in time. In some examples, each stage may output two fine phase signals that have complimentary phases. VCO 1106 may include any suitable number of stages configured to output any suitable number of fine phase signals (e.g., eight stages that output sixteen fine phase signals). The duration of a fine phase signal pulse depends on the oscillator frequency of VCO 1106 and the total number of fine phase signals. For example, if the oscillator frequency is 1 gigahertz (GHz) and the total number of fine phase signals is sixteen, the duration of a pulse included in a fine phase signal is 1 GHz/16, which is 62.5 picoseconds (ps). As described herein, these fine phase signals may provide precision timing circuit 1006 with the ability to adjust a phase (i.e., temporal position) of a timing pulse with relatively fine resolution.

Feedback divider 1108 is configured to be clocked by a single fine phase signal included in the plurality of fine phase signals output by VCO 1106 and have a plurality of feedback divider states during the PLL feedback period. The number of feedback divider states depends on the oscillator frequency of VCO 1106 and the frequency of the reference clock. For example, if the oscillator frequency is 1 gigahertz (GHz) and the reference clock has a frequency of 50 MHz, the number of feedback divider states is equal to 1 GHz/50 MHz, which is equal to 20 feedback divider states. As described herein, these feedback divider states may provide precision timing circuit 1006 with the ability to adjust a phase (i.e., temporal position) of a timing pulse with relatively course resolution.

Feedback divider 1108 may be implemented by any suitable circuitry. In some alternative examples, feedback divider 1108 is at least partially integrated into precision timing circuit 1006.

As shown, the fine phase signals output by VCO 1106 and state information (e.g., signals and/or data) representative of the feedback divider states within feedback divider 1108 are input into precision timing circuit 1006. Precision timing circuit 1006 may be configured to generate a timing pulse and set, based on a combination of one of the fine phase signals and one of the feedback dividers states, a temporal position of the timing pulse within the PLL feedback period. For example, if there are N total fine phase signals and M total feedback divider states, precision timing circuit 1006 may set the temporal position of the timing pulse to be one of N times M possible temporal positions within the PLL feedback period. To illustrate, if N is 16 and M is 20, and if the duration of a pulse included in a fine phase signal is 62.5 ps, the temporal position of the timing pulse may be set to be one of 320 possible positions in 62.5 ps steps.

The timing pulse generated by precision timing circuit 1006 may be used within optical measurement system 100 in any suitable manner. For example, the timing pulse may be configured to trigger a start (e.g., a rising edge) of an output pulse used by a component within optical measurement system 100. Alternatively, the timing pulse may be configured to trigger an end (e.g., a falling edge) of an output pulse used by a component within optical measurement system 100. Alternatively, the timing pulse itself may be provided for use as an output pulse used by a component within optical measurement system 100. In some examples, precision timing circuit 1006 may generate multiple timing pulses each used for a different purpose within optical measurement system 100. PLL circuit based architecture 1008 is described in more detail in U.S. Provisional Patent Application No. 63/027,011, filed May 19, 2020, and incorporated herein by reference in its entirety.

In some examples, processing unit 806 may use the output pulses generated by precision timing circuit 1006 to characterize a timing uncertainty of TDC 1002 by using the output pulses to characterize one or more nonlinearities of TDC 1002. This may be performed in any suitable manner.

For example, processing unit 806 may direct precision timing circuit 1006 to apply the output pulses to TDC 1002 by directing multiplexer 1012 to pass the output pulses to TDC 1002 by way of output buffer 1014 and by directing precision timing circuit 1006 to sweep the output pulses across a plurality of temporal positions. Processing unit 806 may generate characterization data for TDC 1002 by generating, based on timestamp symbols recorded by TDC 1002 in response to the output pulses, data representative of a transfer curve that represents a characterization of one or more nonlinearities of TDC 1002. In some examples, this characterization may be performed while optical measurement system 100 is operating in a high resolution mode in which precision timing circuit 1006 is configured to sweep the output pulses across a plurality of relatively finely spaced temporal positions.

Figure 12:
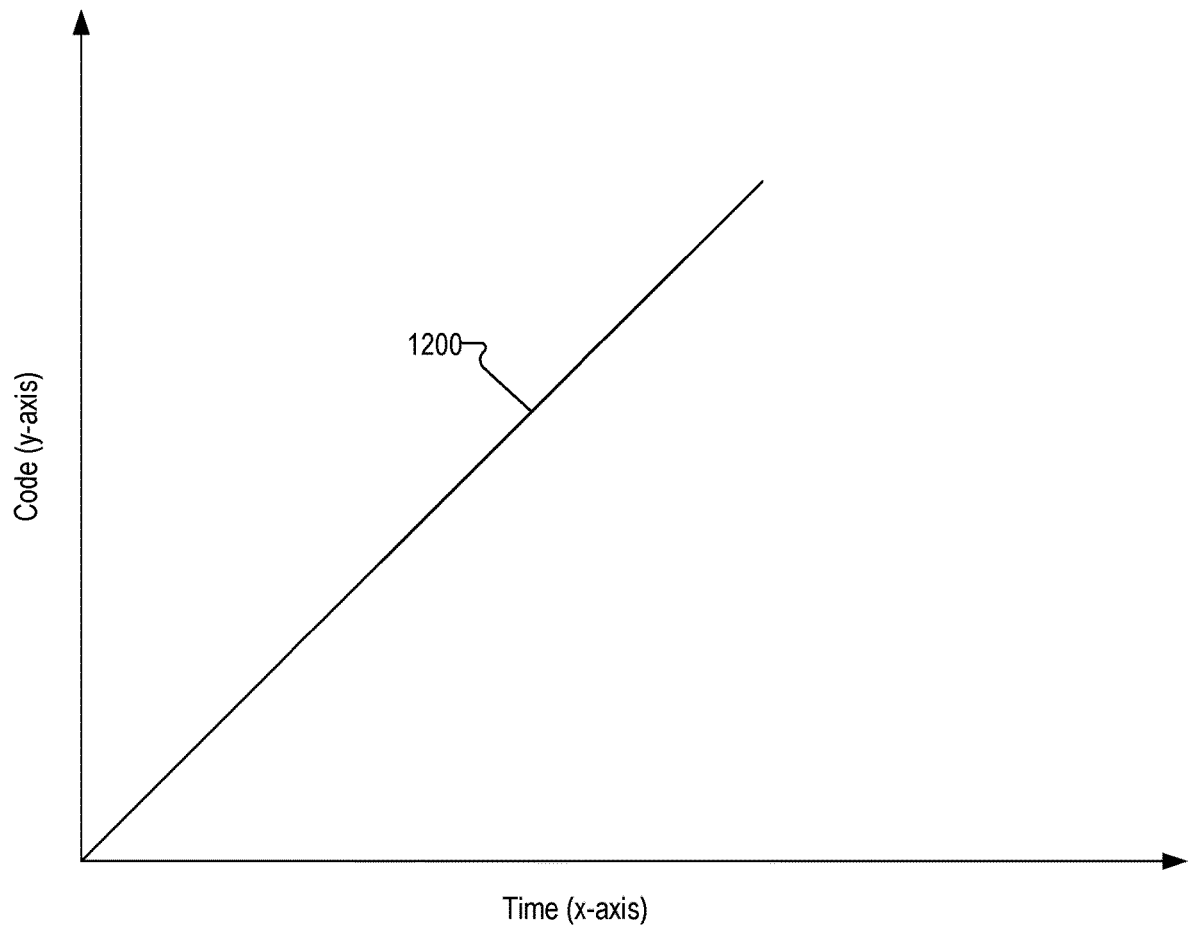
FIG. 12 shows an exemplary transfer curve.

FIG. 12 shows an exemplary transfer curve 1200 that may be generated by processing unit 806 and that represents a characterization of one or more nonlinearities of TDC 1002. As shown, transfer curve 1200 represents a plot of actual temporal positions (the x-axis labeled "Time") of the output pulses versus timestamp symbols recorded by TDC 1002 (the y-axis labeled "Code"). Ideally, the actual temporal positions of the output pulses and the timestamp symbols have a one to one correspondence, thereby resulting in linear transfer curve 1200, as shown in FIG. 12. However, one or more nonlinearities of TDC 1002 may cause transfer curve 1200 to have one or more irregularities (e.g., one or more nonlinearities).

Based on characterization data that indicates that transfer curve 1200 has one or more irregularities, processing unit 806 may perform one or more suitable actions. For example, processing unit 806 may compensate for the one or more irregularities in transfer curve 1200. To illustrate, processing unit 806 may program one or more digital offsets into timestamp symbols recorded by TDC 1002 to cause transfer curve 1200 to be linear.

Figure 13:
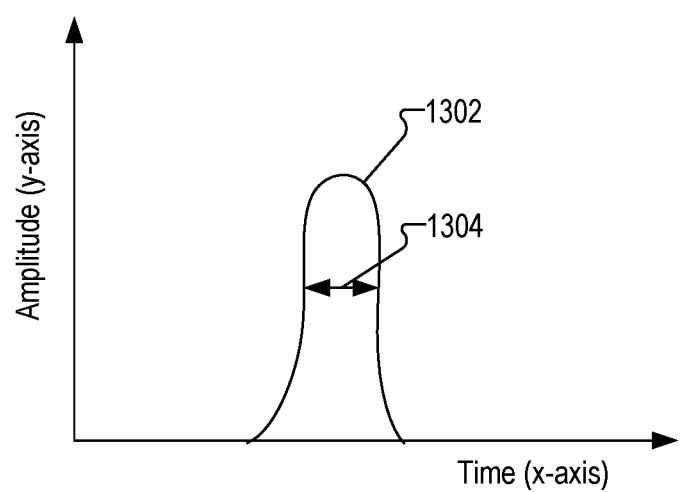
FIG. 13 shows an exemplary impulse response function.

Additionally or alternatively, processing unit 806 may use the output pulses generated by precision timing circuit 1006 to characterize a timing uncertainty of TDC 1002 by using the output pulses to characterize an impulse response function (e.g., an electrical impulse response function, also referred to as jitter) of TDC 1002. FIG. 13 shows an exemplary impulse response function 1302 that may be associated with TDC 1002 (or any other component within optical measurement system 100 that is being characterized). A time spread 1304 of impulse response function 1302 represents time uncertainty, which adds time uncertainty to an overall histogram measurement. In other words, the more time uncertainty in an impulse response function, the broader the histogram will be independent of the actual signal being measured.

Processing unit 806 may characterize an impulse response function of TDC 1002 in any suitable manner. For example, processing unit 806 may be configured to direct precision timing circuit 1006 to generate output pulses each having the same programmable temporal position within the PLL feedback period of PLL circuit 1004. Processing unit 806 may further direct precision timing circuit 1006 to apply the output pulses to TDC 1002 (e.g., by way of output buffer 1012). Any suitable plurality of output pulses may be applied to TDC 1002 as may serve a particular implementation. Processing unit 806 may generate characterization data for TDC 1002 by determining a variation in timestamp symbols recorded by TDC 1002 in response to the output pulses and generating, based on the determined variation, data representative of a characterization of an impulse response function of TDC 1002.

Based on characterization data representative of the impulse response function of TDC 1002, processing unit 806 may perform one or more suitable actions. For example, processing unit 806 may rate TDC 1002 based on the characterization data. This rating may be compared to other TDCs (e.g., in the same TDC array). In some examples, if the rating of TDC 1002 is outside a predetermined range of values (e.g., if the rating value deviates too much from a range of rating values for other TDCs in the same TDC array), thereby indicating that TDC 1002 has a relatively poor impulse response function, TDC 1002 and its corresponding photodetector may be disabled so as to not skew an overall histogram generated by optical measurement system 100. TDC 1002 and its corresponding photodetector may be disabled in any suitable manner. For example, processing unit 806 may disable a power supply for TDC 1002 and/or its corresponding photodetector, transmit a control signal to TDC 1002 and/or its corresponding photodetector that turns off or disables TDC 1002 and/or its corresponding photodetector, and/or abstain from transmitting a gate on pulse to the photodetector.

Processing unit 806 may be configured to additionally or alternatively characterize a timing uncertainty (e.g., an impulse response function, also referred to as jitter) of a photodetector included in optical measurement system 100.

Figure 14:
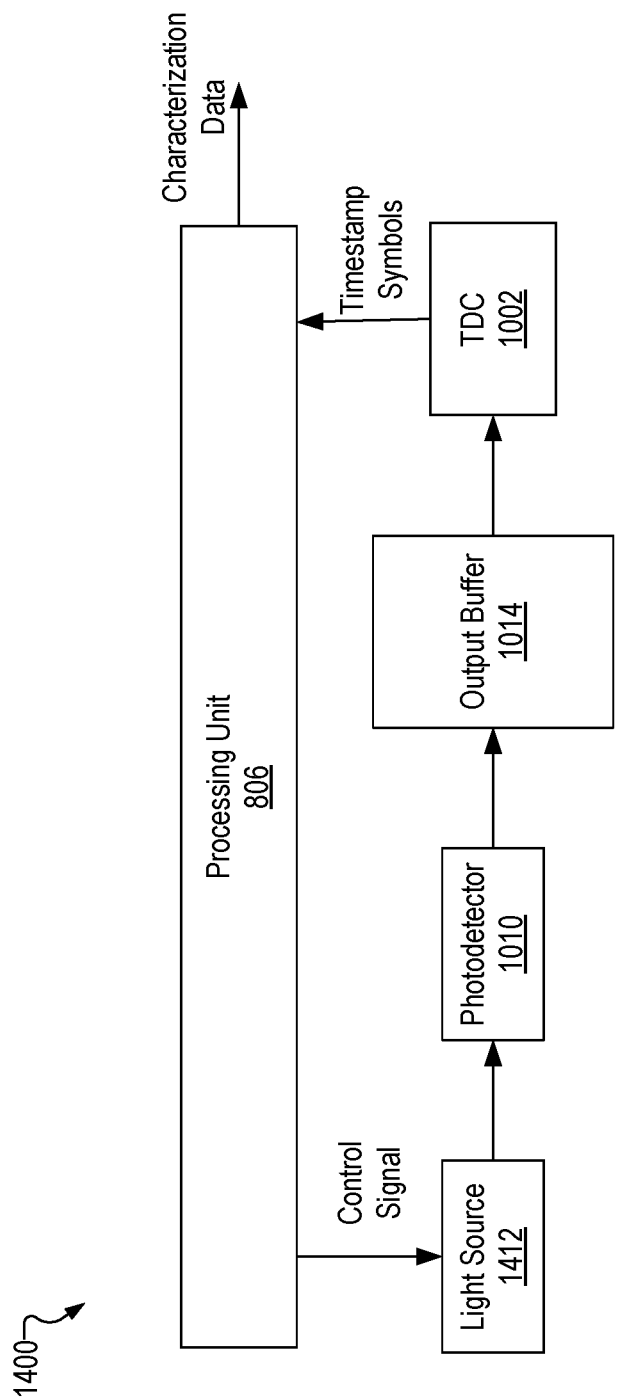
FIGS. 14-15 show exemplary implementations of the configuration shown in FIG. 8.

For example, FIG. 14 shows an exemplary implementation 1400 of configuration 800 in which component 802 is implemented by photodetector 1010 and signal generator 804 is implemented by a light source 1412 configured to generate a plurality of light pulses. Implementation 1400 further includes output buffer 1014 and TDC 1002. In some alternative embodiments, implementation 1400 further includes multiplexer 1012 so that processing unit 806 may selectively switch between characterizing photodetector 1010 and TDC 1002.

In implementation 1400, processing unit 806 may be configured to direct light source 1412 (e.g., by transmitting a control signal to light source 1412) to output a plurality of light pulses. Photodetector 1010 is configured to output a photodetector output pulse each time photodetector 1010 detects a photon from the light pulses. TDC 1002 is configured to record a timestamp symbol each time TDC 1002 detects an occurrence of the photodetector output pulse. Processing unit 806 may generate characterization data for photodetector 1010 by determining a variation in the timestamp symbols recorded by TDC 1002 and generating, based on the variation in the timestamp symbols recorded by TDC 1002, data representative of a characterization of an impulse response function of photodetector 1010.

Based on characterization data representative of the impulse response function of photodetector 1010, processing unit 806 may perform one or more suitable actions. For example, processing unit 806 may rate photodetector 1010 based on the characterization data. This rating may be compared to other photodetectors (e.g., in the same photodetector array). In some examples, if the rating of photodetector 1010 is outside a predetermined range of values (e.g., if the rating value deviates too much from a range of rating values for other photodetectors in the same photodetector array), thereby indicating that photodetector 1010 has a relatively poor impulse response function, photodetector 1010 may be disabled so as to not skew an overall histogram generated by optical measurement system 100. Photodetector 1010 may be disabled in any suitable manner. For example, processing unit 806 may disable a power supply for photodetector 1010, transmit a control signal to photodetector 1010 that turns off or disables photodetector 1010, and/or abstain from transmitting a gate on pulse to photodetector 1010.

In configurations in which outputs of many TDCs (e.g., each TDC included in an array of TDCs) are combined into a single histogram, processing unit 806 may be configured to isolate each TDC/photodetector pair so that only one TDC/photodetector pair is active at any given time. This may allow a timing uncertainty of each individual TDC and/or photodetector to be characterized. For example, while processing unit 806 characterizes a timing uncertainty of TDC 1002 and/or photodetector 1010, processing unit 806 may disable other TDCs within an array of TDCs (e.g., TDC array 704) of which TDC 1002 is a part and other photodetectors within an array of photodetectors (e.g., photodetector array 702) of which photodetector 1010 is a part. This may be performed in any suitable manner.

The timing uncertainty characterizations described herein may be performed by processing unit 806 at any suitable time. For example, processing unit 806 may be configured to place optical measurement system 100 in a calibration mode (e.g., during a startup procedure for optical measurement system 100) and perform one or more timing uncertainty characterizations described herein while optical measurement system 100 is in the calibration mode.

Figure 15:
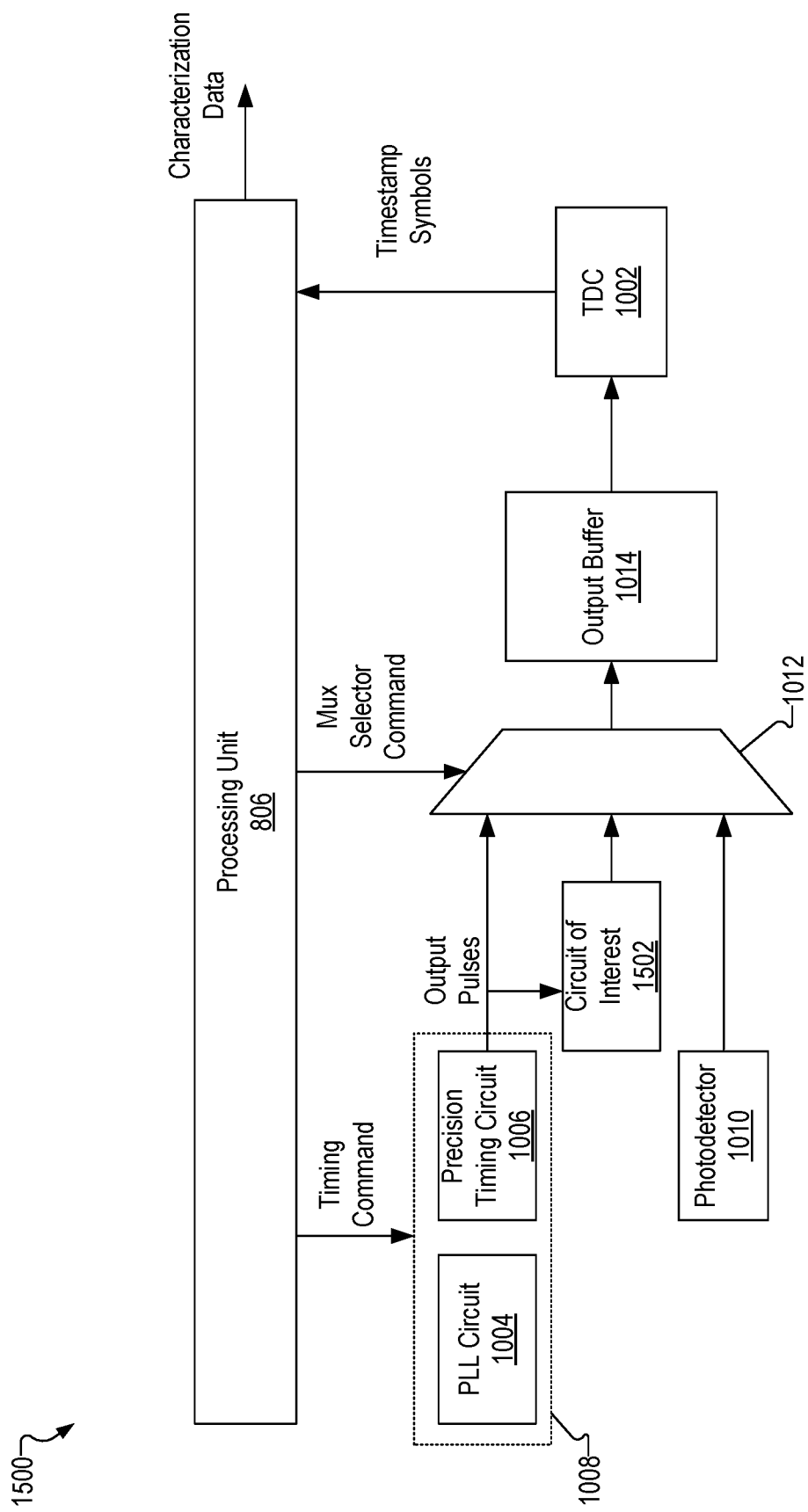

The systems, circuits, and methods described herein may be used to characterize a timing uncertainty of any other component included in optical measurement system 100 as may serve a particular implementation. For example, FIG. 15 illustrates an exemplary implementation 1500 of configuration 800 in which processing unit 806 is configured to use output pulses generated by precision timing circuit 1006 to characterize a timing uncertainty of a circuit of interest 1502. Implementation 1500 is similar to implementation 1000, except that in implementation 1500, multiplexer 1012 is configured to selectively pass output pulses, an output of circuit of interest 1502, or an output of photodetector 1010 to TDC 1002 by way of output buffer 1014. Circuit of interest 1502 may include any suitable circuit and/or electrical path within a detector that includes a photodetector.

As mentioned, optical measurement system 100 may be at least partially wearable by a user. For example, optical measurement system 100 may be implemented by a wearable device configured to be worn by a user (e.g., a head-mountable component configured to be worn on a head of the user). The wearable device may include one or more photodetectors, modules, and/or any of the other components described herein. In some examples, one or more components (e.g., processing unit 806, processor 108, controller 112, etc.) may not be included in the wearable device and/or included in a separate wearable device than the wearable device in which the one or more photodetectors are included. In these examples, one or more communication interfaces (e.g., cables, wireless interfaces, etc.) may be used to facilitate communication between the various components.

FIGS. 16-21 illustrate embodiments of a wearable device 1600 that includes elements of the optical detection systems described herein. In particular, the wearable devices 1600 shown in FIGS. 16-21 include a plurality of modules 1602, similar to the modules shown in FIG. 6 as described herein. For example, each module 1602 may include a source (e.g., source 604) and a plurality of detectors (e.g., detectors 606-1 through 606-6). The wearable devices 1600 may each also include a controller (e.g., controller 112) and a processor (e.g., processor 108) and/or be communicatively connected to a controller and processor. In general, wearable device 1600 may be implemented by any suitable headgear and/or clothing article configured to be worn by a user. The headgear and/or clothing article may include batteries, cables, and/or other peripherals for the components of the optical measurement systems described herein.

Figure 16:
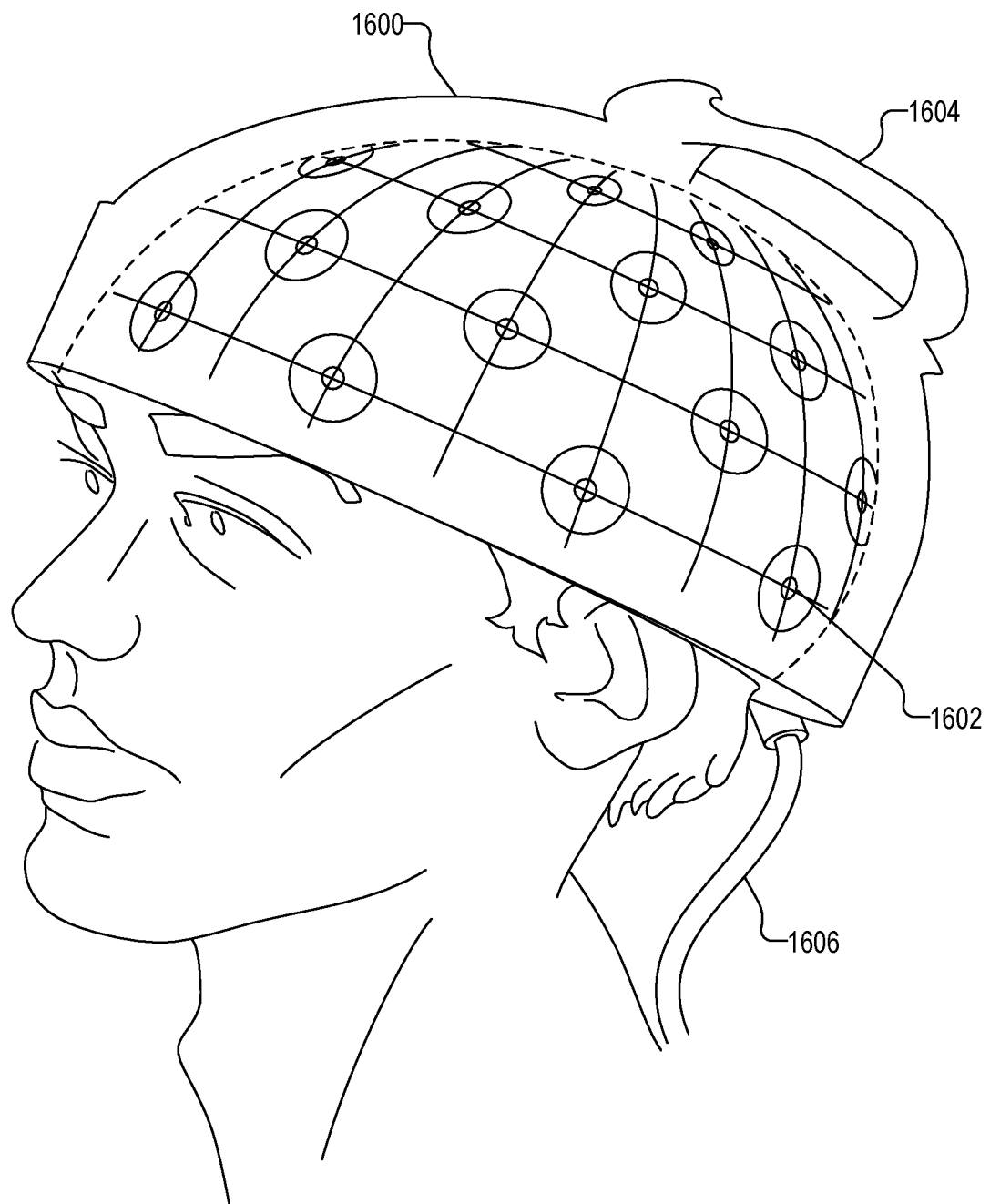
FIGS. 16-21 illustrate embodiments of a wearable device that includes elements of the optical detection systems described herein.
Figure 17:
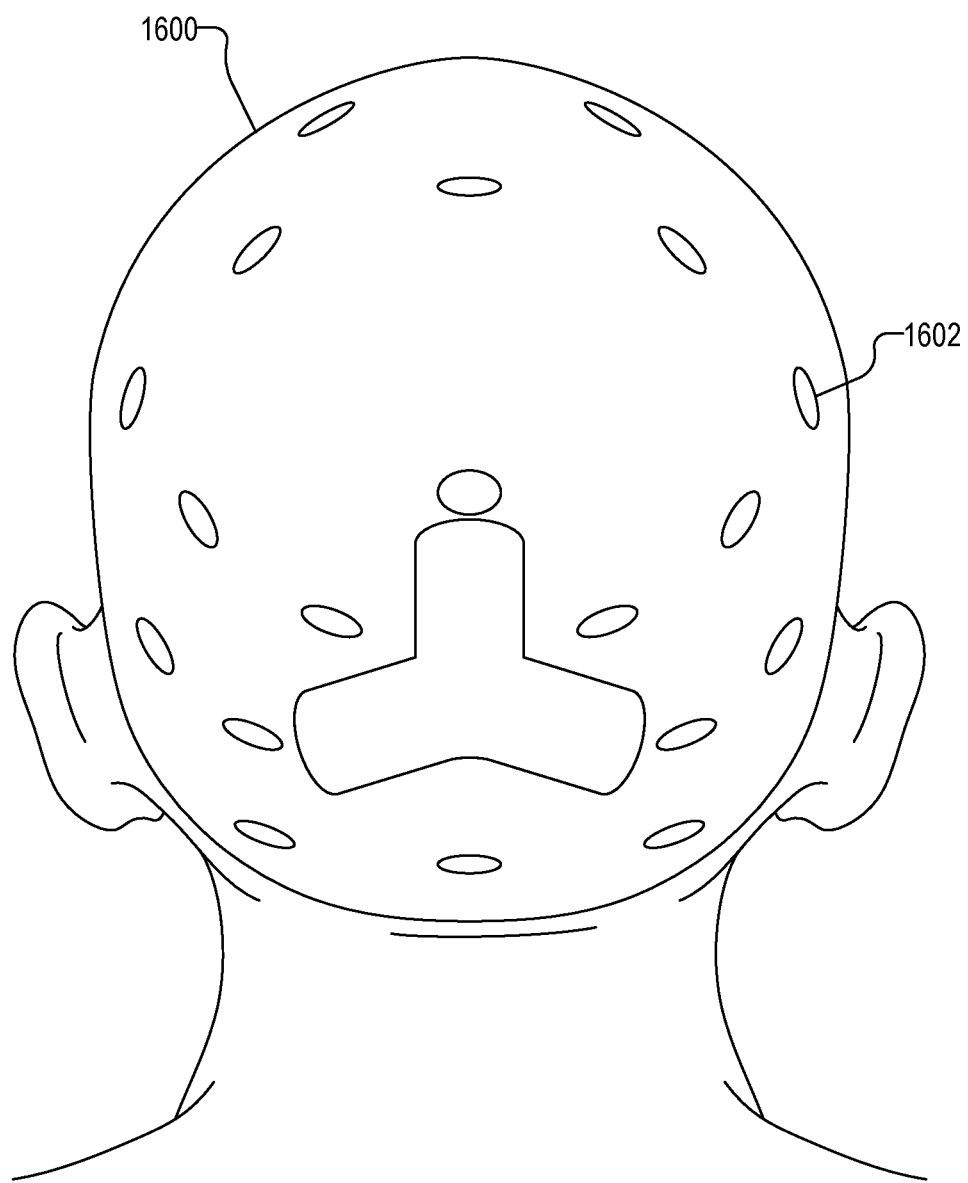
Figure 18:
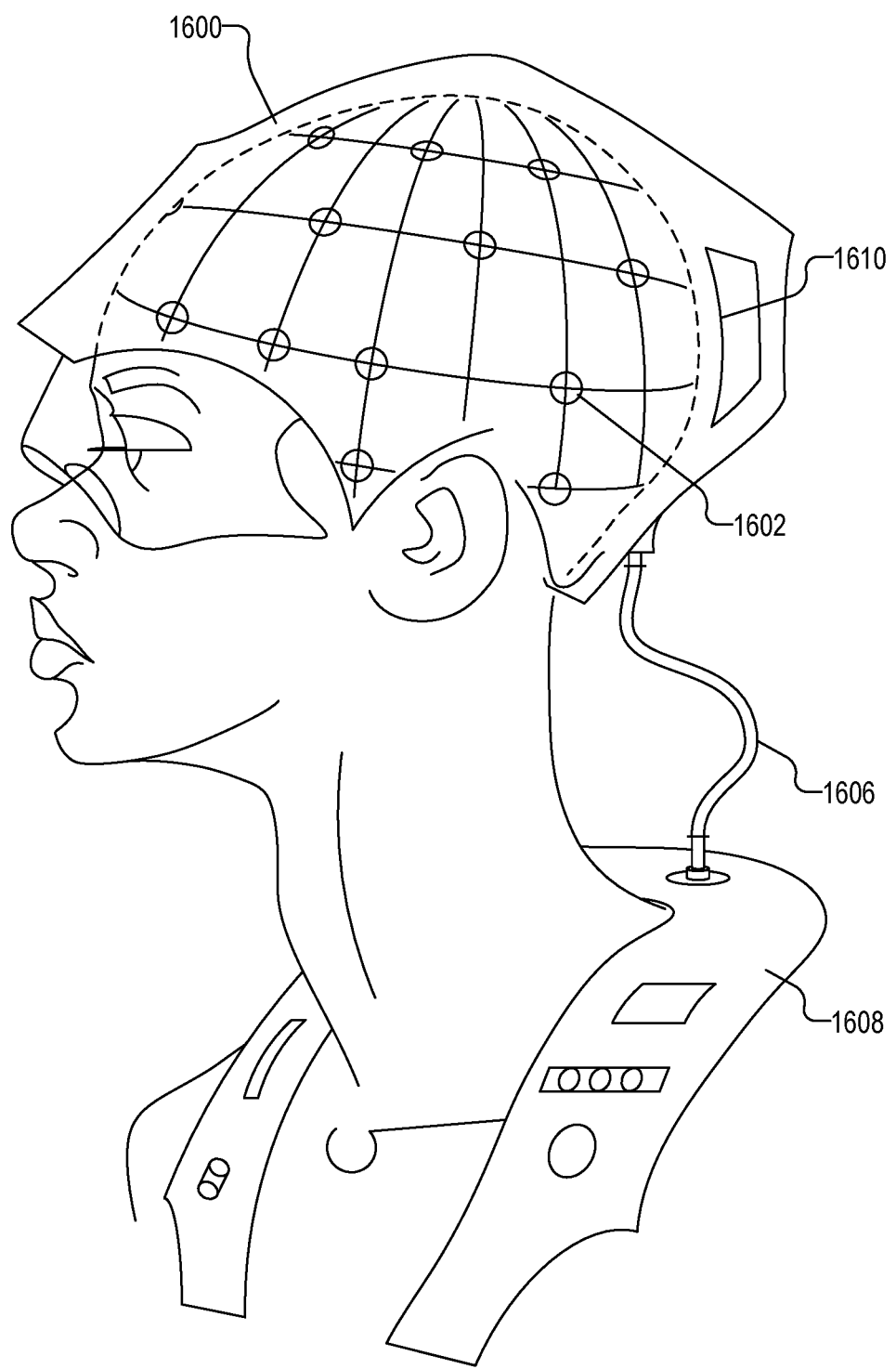

FIG. 16 illustrates an embodiment of a wearable device 1600 in the form of a helmet with a handle 1604. A cable 1606 extends from the wearable device 1600 for attachment to a battery or hub (with components such as a processor or the like). FIG. 17 illustrates another embodiment of a wearable device 1600 in the form of a helmet showing a back view. FIG. 18 illustrates a third embodiment of a wearable device 1600 in the form of a helmet with the cable 1606 leading to a wearable garment 1608 (such as a vest or partial vest) that can include a battery or a hub. Alternatively or additionally, the wearable device 1600 can include a crest 1610 or other protrusion for placement of the hub or battery.

Figure 19:
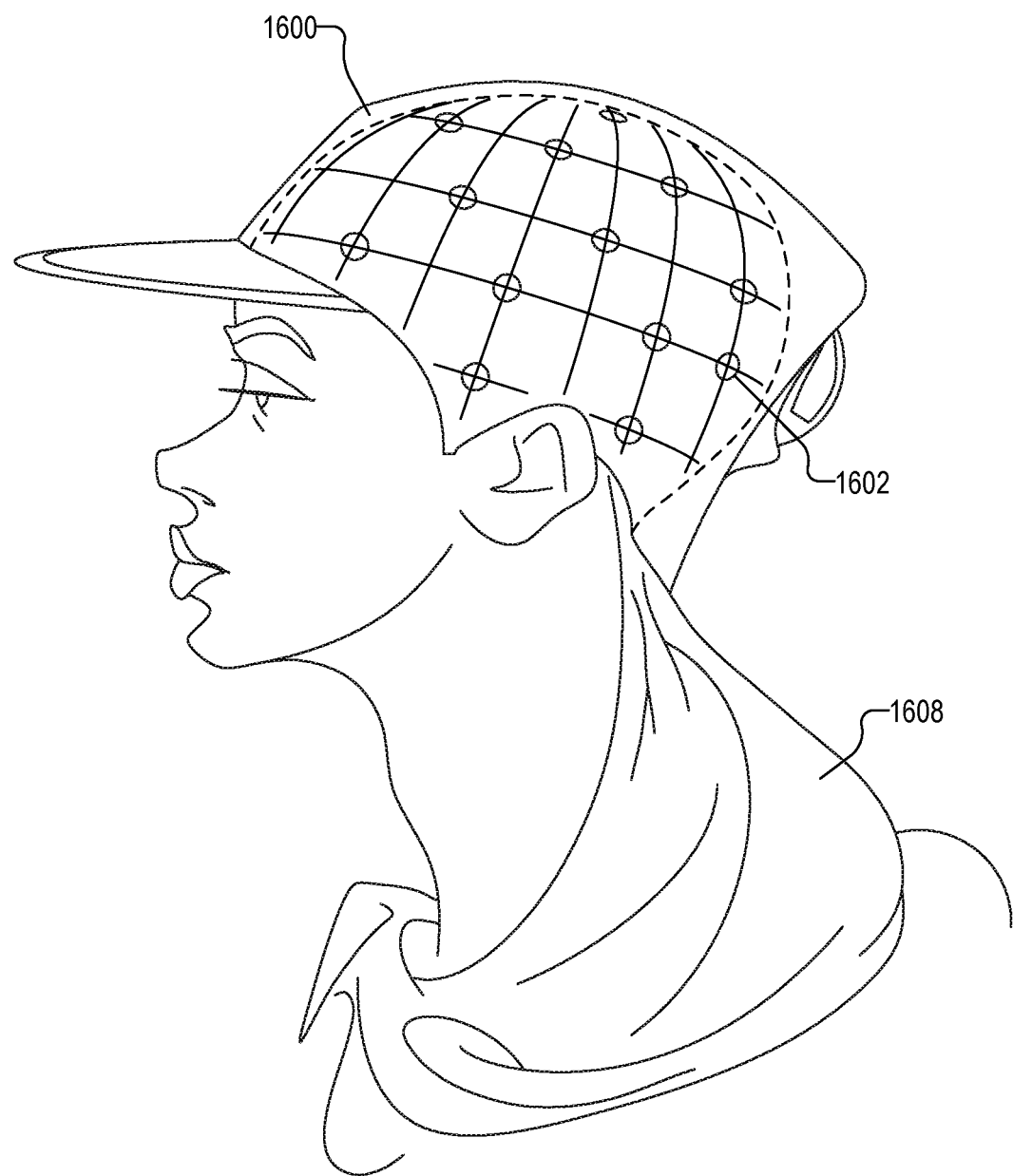
Figure 20:
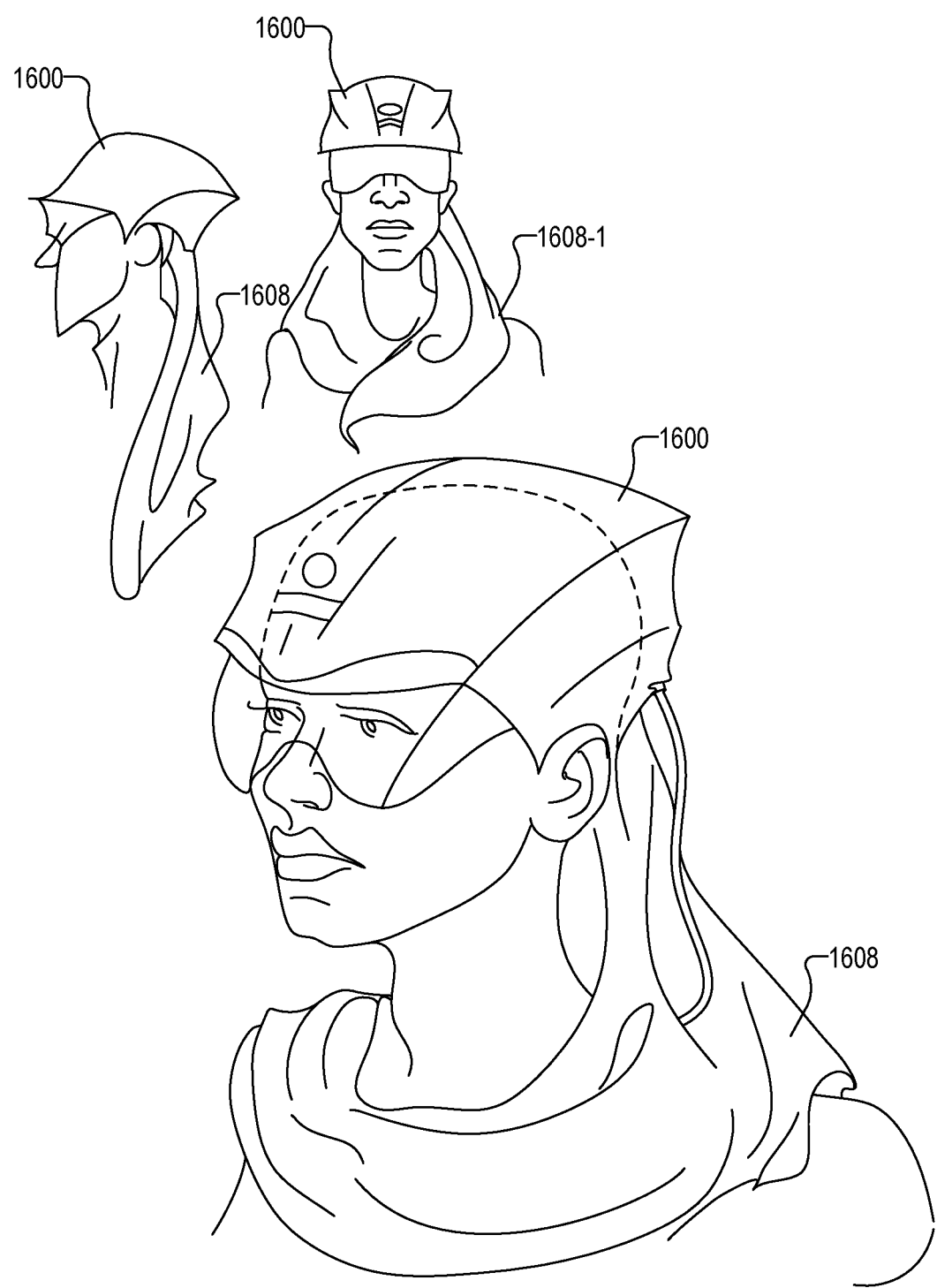
Figure 21:
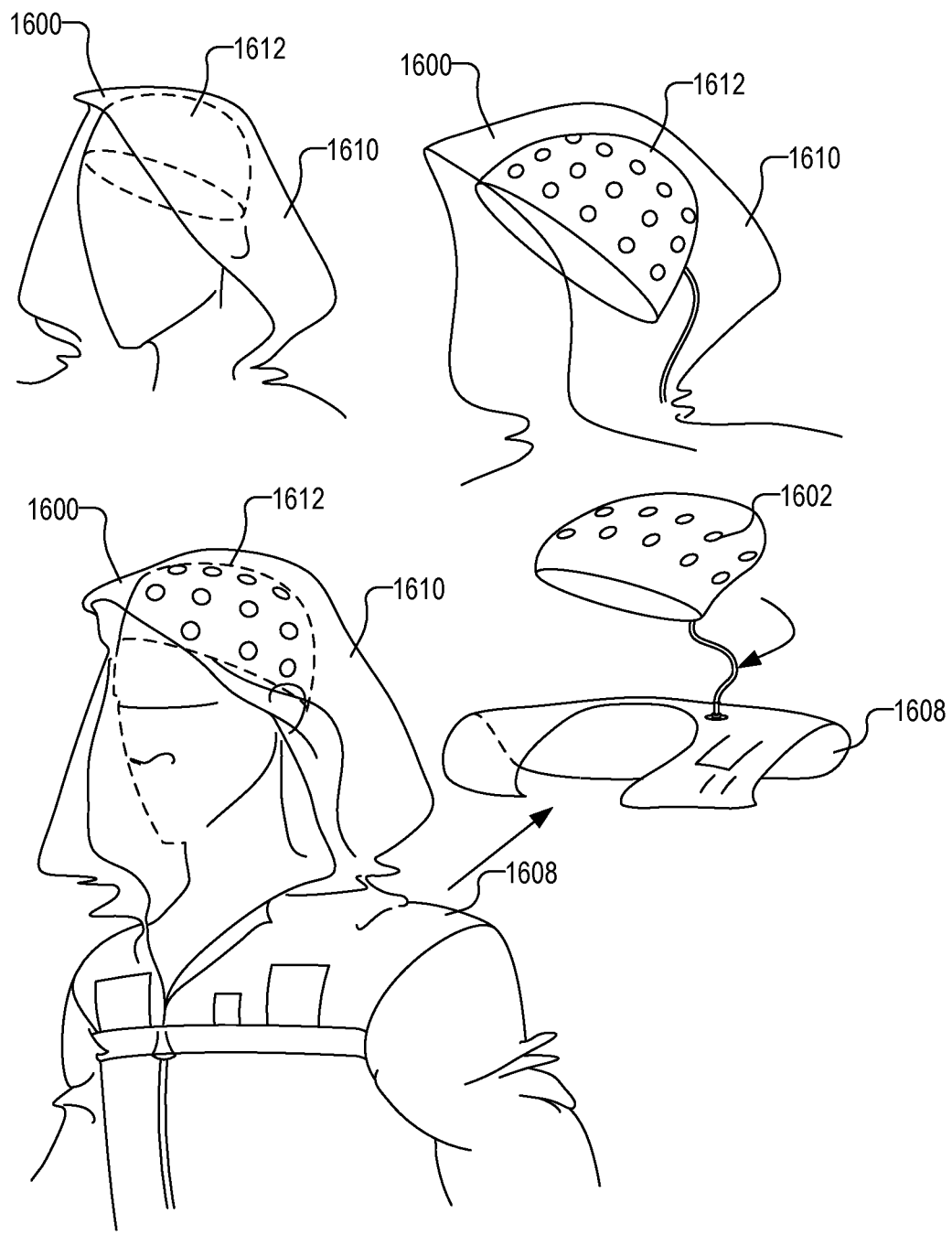

FIG. 19 illustrates another embodiment of a wearable device 1600 in the form of a cap with a wearable garment 1608 in the form of a scarf that may contain or conceal a cable, battery, and/or hub. FIG. 20 illustrates additional embodiments of a wearable device 1600 in the form of a helmet with a one-piece scarf 1608 or two-piece scarf 1608-1. FIG. 21 illustrates an embodiment of a wearable device 1600 that includes a hood 1610 and a beanie 1612 which contains the modules 1602, as well as a wearable garment 1608 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 22:
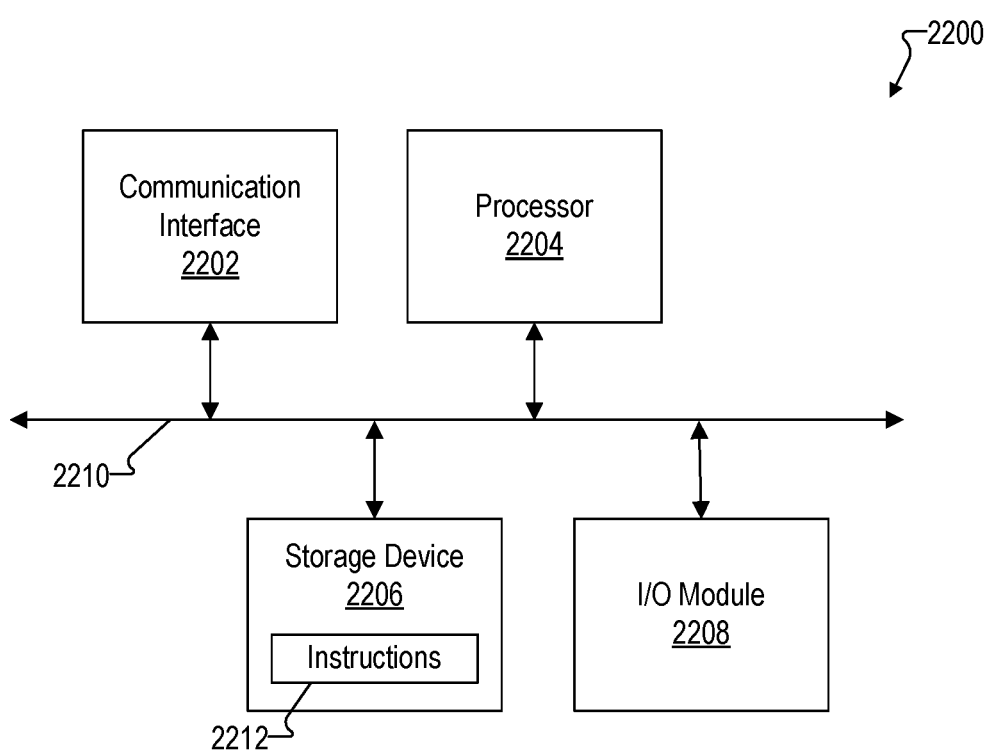
FIG. 22 illustrates an exemplary computing device.

FIG. 22 illustrates an exemplary computing device 2200 that may be specifically configured to perform one or more of the processes described herein. Any of the systems, units, computing devices, and/or other components described herein may be implemented by computing device 2200.

As shown in FIG. 22, computing device 2200 may include a communication interface 2202, a processor 2204, a storage device 2206, and an input/output ("I/O") module 2208 communicatively connected one to another via a communication infrastructure 2210. While an exemplary computing device 2200 is shown in FIG. 22, the components illustrated in FIG. 22 are not intended to be limiting. Additional or alternative components may be used in other embodiments. Components of computing device 2200 shown in FIG. 22 will now be described in additional detail.

Communication interface 2202 may be configured to communicate with one or more computing devices. Examples of communication interface 2202 include, without limitation, a wired network interface (such as a network interface card), a wireless network interface (such as a wireless network interface card), a modem, an audio/video connection, and any other suitable interface.

Processor 2204 generally represents any type or form of processing unit capable of processing data and/or interpreting, executing, and/or directing execution of one or more of the instructions, processes, and/or operations described herein. Processor 2204 may perform operations by executing computer-executable instructions 2212 (e.g., an application, software, code, and/or other executable data instance) stored in storage device 2206.

Storage device 2206 may include one or more data storage media, devices, or configurations and may employ any type, form, and combination of data storage media and/or device. For example, storage device 2206 may include, but is not limited to, any combination of the non-volatile media and/or volatile media described herein. Electronic data, including data described herein, may be temporarily and/or permanently stored in storage device 2206. For example, data representative of computer-executable instructions 2212 configured to direct processor 2204 to perform any of the operations described herein may be stored within storage device 2206. In some examples, data may be arranged in one or more databases residing within storage device 2206.

I/O module 2208 may include one or more I/O modules configured to receive user input and provide user output. I/O module 2208 may include any hardware, firmware, software, or combination thereof supportive of input and output capabilities. For example, I/O module 2208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2208 is configured to provide graphical data to a display for presentation to a user. The graphical data may be representative of one or more graphical user interfaces and/or any other graphical content as may serve a particular implementation.

Figure 23:
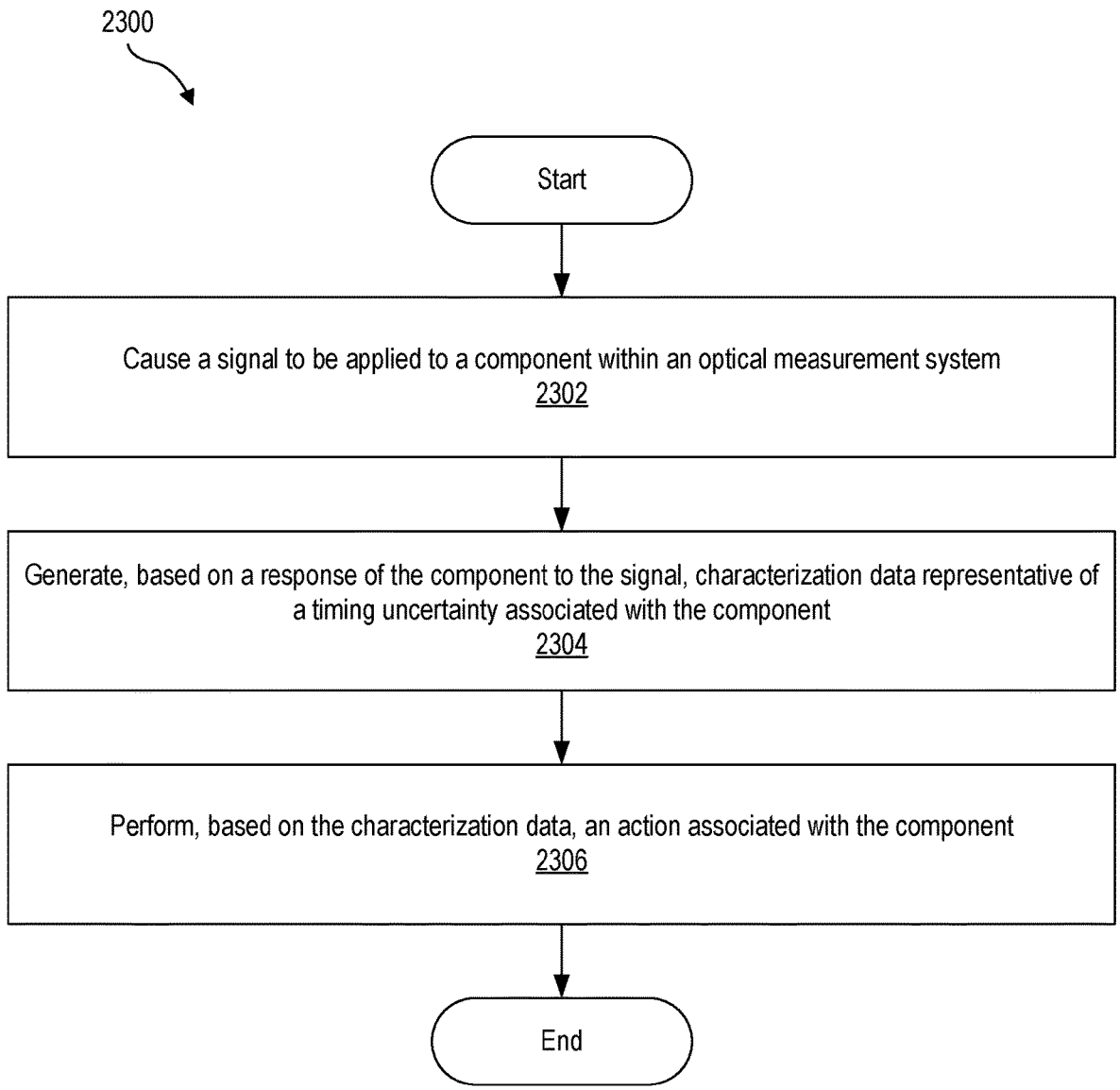
FIG. 23 illustrates an exemplary method.

FIG. 23 illustrates an exemplary method 2300 that may be performed by a processing unit as described herein. While FIG. 23 illustrates exemplary operations according to one embodiment, other embodiments may omit, add to, reorder, and/or modify any of the operations shown in FIG. 23. Each of the operations shown in FIG. 23 may be performed in any of the ways described herein.

In operation 2302, a processing unit causes a signal to be applied to a component (e.g., TDC and its corresponding photodetector, photodetector(s) and/or any other circuit of interest) within an optical measurement system.

In operation 2304, the processing unit generates, based on a response of the component to the signal, characterization data representative of a timing uncertainty associated with the component.

In operation 2306, the processing unit performs, based on the characterization data, an action associated with the component. The action may include compensating for the timing uncertainty, rating the component, disabling the component, and/or any other suitable action.

An exemplary optical measurement system includes a signal generator configured to generate a signal and a processing unit configured to direct the signal generator to apply the signal to a component within the optical measurement system, generate, based on a response of the component to the signal, characterization data representative of a timing uncertainty associated with the component, and perform, based on the characterization data, an action associated with the component.

An exemplary optical measurement system includes a phase lock loop (PLL) circuit having a PLL feedback period, a precision timing circuit configured to generate output pulses having programmable temporal positions within the PLL feedback period, and a processing unit configured to use the output pulses to generate characterization data representative of a characterization of a timing uncertainty associated with a component of the optical measurement system and perform, based on the characterization data, an action associated with the component.

An exemplary system includes a memory storing instructions and a processor communicatively coupled to the memory and configured to execute the instructions to cause a signal to be applied to a component within an optical measurement system; generate, based on a response of the component to the signal, characterization data representative of a timing uncertainty associated with the component; and perform, based on the characterization data, an action associated with the component.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
a signal generator configured to generate a signal; and
a processing unit configured to
  direct the signal generator to apply the signal to a component within the optical measurement system,
  generate, based on a response of the component to the signal, characterization data representative of a timing uncertainty associated with the component, and
  perform, based on the characterization data, an action associated with the component.

2. The optical measurement system of claim 1, further comprising:
a photodetector; and
a time-to-digital converter (TDC) configured to measure a time difference between an occurrence of a light pulse and an occurrence of a photodetector output pulse generated by the photodetector, the photodetector output pulse indicating that the photodetector has detected a photon from the light pulse after the light pulse is scattered by a target;
wherein the component is one or more of the photodetector or the TDC.

3. The optical measurement system of claim 2, wherein:
the component is the TDC;
the signal generator comprises
  a phase lock loop (PLL) circuit having a PLL feedback period, and
  a precision timing circuit configured to generate output pulses having programmable temporal positions within the PLL feedback period, the signal comprising a sequence of the output pulses;
the directing of the signal generator to apply the signal to the component comprises directing the precision timing circuit to sweep the output pulses across a plurality of temporal positions; and
the generating of the characterization data comprises generating, based on timestamp symbols recorded by the TDC in response to the output pulses, data representative of a transfer curve that represents a characterization of one or more nonlinearities of the TDC.

4. The optical measurement system of claim 3, wherein the performing of the action associated with the component comprises compensating for one or more irregularities in the transfer curve.

5. The optical measurement system of claim 3, wherein:
the TDC is included in an array of TDCs; and
the processing unit is configured to disable other TDCs within the array of TDCs while the signal is being applied to the TDC.

6. The optical measurement system of claim 2, further comprising a multiplexer configured to selectively pass, to the TDC, the signal or a photodetector output pulse generated by the photodetector.

7. The optical measurement system of claim 6, wherein:
the component is the TDC;
the processing unit is configured to direct the multiplexer to pass the signal to the TDC.

8. The optical measurement system of claim 6, further comprising an output buffer in series with an output of the multiplexer and the TDC, wherein the signal or the photodetector output pulse is passed to the TDC by way of the output buffer.

9. The optical measurement system of claim 2, wherein:
the component is the TDC;
the signal generator comprises
  a phase lock loop (PLL) circuit having a PLL feedback period, and
  a precision timing circuit configured to generate output pulses each having a same programmable temporal position within the PLL feedback period, the signal comprising a sequence of the output pulses;
the directing of the signal generator to apply the signal to the component comprises directing the precision timing circuit to apply the output pulses to the TDC; and
the generating of the characterization data comprises generating, based on a variation in timestamp symbols recorded by the TDC in response to the output pulses, data representative of a characterization of an impulse response function of the TDC.

10. The optical measurement system of claim 9, wherein:
the TDC is included in an array of TDCs; and
the processing unit is configured to disable other TDCs within the array of TDCs while the signal is being applied to the TDC.

11. The optical measurement system of claim 9, wherein the performing of the action associated with the component comprises rating the TDC based on the characterization data.

12. The optical measurement system of claim 2, wherein:
the component is the photodetector;
the signal generator comprises a light source configured to output a plurality of light pulses;
the directing of the signal generator to apply the signal to the component comprises directing the light source to output the light pulses; and
the photodetector is configured to output a photodetector output pulse each time the photodetector detects a photon from the light pulses;

the TDC is configured to record a timestamp symbol each time the TDC detects an occurrence of the photodetector output pulse;

the generating of the characterization data comprises generating, based on a variation in the timestamp symbols recorded by the TDC, data representative of a characterization of an impulse response function of the photodetector.

13. The optical measurement system of claim 12, wherein the performing of the action associated with the component comprises rating the photodetector based on the characterization data.

14. The optical measurement system of claim 12, wherein the performing of the action associated with the component comprises:
   determining that a value of the characterization data is outside a predetermined range of values; and
   disabling, in response to the determining that the value is outside the predetermined range of values, the photodetector.

15. The optical measurement system of claim 12, wherein:
   the photodetector is included in an array of photodetectors; and
   the processing unit is configured to disable other photodetectors within the array of photodetectors while the light pulses are being applied to the photodetector.

16. The optical measurement system of claim 2, wherein the photodetector comprises a single photon avalanche diode (SPAD).

17. The optical measurement system of claim 1, further comprising a head-mountable component configured to be worn on a head of a user, wherein one or more of the signal generator or the processing unit are included in the head-mountable component.

18. The optical measurement system of claim 1, wherein:
   the processing unit is configured to place the optical measurement system in a calibration mode; and
   the directing, generating, and performing are performed while the optical measurement system is in the calibration mode.

* * * * *